(12) United States Patent
Vizanski

(10) Patent No.: US 9,855,113 B2
(45) Date of Patent: Jan. 2, 2018

(54) METHOD FOR TEETH RESTORATION AND A TEETH MATRIX

(76) Inventor: Amiram Vizanski, Herzliya (IL)

( * ) Notice: Subject to any disclaimer, the term of this patent is extended or adjusted under 35 U.S.C. 154(b) by 693 days.

(21) Appl. No.: 12/614,458

(22) Filed: Nov. 9, 2009

(65) Prior Publication Data
US 2010/0316976 A1    Dec. 16, 2010

Related U.S. Application Data

(63) Continuation-in-part of application No. PCT/IL2008/000650, filed on May 11, 2008.

(60) Provisional application No. 60/916,814, filed on May 9, 2007, provisional application No. 60/948,466, filed on Jul. 8, 2007.

(51) Int. Cl.
| | |
|---|---|
| *A61C 5/77* | (2017.01) |
| *A61C 13/00* | (2006.01) |
| *A61C 5/73* | (2017.01) |
| *A61C 5/70* | (2017.01) |

(52) U.S. Cl.
CPC ............. *A61C 5/77* (2017.02); *A61C 5/70* (2017.02); *A61C 5/73* (2017.02); *A61C 13/0004* (2013.01)

(58) Field of Classification Search
CPC ........................................... A61C 5/77
USPC ................................................. 264/19
See application file for complete search history.

(56) References Cited

U.S. PATENT DOCUMENTS

| | | | | |
|---|---|---|---|---|
| 4,828,117 A | * | 5/1989 | Panzera et al. | 206/63.5 |
| 6,648,645 B1 | * | 11/2003 | MacDougald et al. | 433/223 |
| 2003/0203339 A1 | * | 10/2003 | Chilibeck | 433/218 |

FOREIGN PATENT DOCUMENTS

EP    1661529    10/2011

\* cited by examiner

*Primary Examiner* — Larry Thrower
(74) *Attorney, Agent, or Firm* — Deborah Gador

(57) ABSTRACT

A method for preparing a dental prosthesis, the method includes: selecting a tooth matrix out of a group of tooth matrices that differ from each other, wherein each tooth matrix comprises an inner cavity; wherein a tooth matrix is has an appearance of a tooth; and attaching at least a wall of the inner cavity of the tooth matrix to an intermediate element that is connected to the prosthesis core, remaining tooth structure or to the implant.

7 Claims, 20 Drawing Sheets

Determining a shape of a tooth matrix out of a group of tooth matrices that includes multiple tooth matrices that differ from each other, wherein each tooth matrix comprises an inner cavity; wherein a tooth matrix has an appearance of a tooth. Wherein the inner cavity is shaped so as to include an intermediate element that is connected to a remaining tooth structure or an implant. 310

Manufacturing, in response to the determination, the tooth matrix. 320

METHOD FOR TEETH RESTORATION AND A TEETH MATRIX

CROSS-REFERENCE TO RELATED APPLICATIONS

This application is a continuation-in-part application of PCT International Application No. PCT/IL2008/000650, International Filing Date May 11, 2008 which claims benefit of U.S. Provisional Patent Application No. 60/916,814, filed May 9, 2007 and U.S. Provisional Patent Application No. 60/948,466, filed Jul. 8, 2007, all of which are incorporated in their entirety herein by reference.

FIELD OF THE INVENTION

This application relates to teeth matrixes, kits and methods for tooth restoration.

BACKGROUND OF THE INVENTION

In dental restoration, a prosthetic is prepared to replace one or more missing, damaged, or unaesthetic looking teeth. Such dental prosthetics include bridges, full crowns and partial crowns. Full and partial crowns are supported by remaining portions of the original tooth or teeth and/or by an abutment and/or dental implants extending from the jaw bone. Bridges are supported by two or more teeth structures adjacent to the missing teeth or solely by implants that replaces the missing tooth root.

The dental prosthesis is generally for functional and aesthetic purpose is made of porcelain, the porcelain is a brittle material and to withstand the occlusal forces it need reinforcing. The reinforcing is generally obtained from a core structure of a hard material such as metals, aluminas (al2o3) zirconium, lava and more core material known to the art. The core structure is then incrementally covered with increments of porcelain slurry made of liquid and porcelain powder to provide outer surface of a tooth that is shaped according to the location in the mouth of the one tooth or more teeth. The surface of restoration is than tooled to provide the outer surface of the restoration in accordance with the appearance of a tooth. Since the preparation of the prosthesis, including the tooling of the prosthesis is performed at a dental laboratory; neither the recipient nor the dentist has any control on the final appearance of the restoration. Due to this situation, the recipient and the dentist expectations often do not adhere with the final appearance of the prosthesis, this lead to dissatisfaction and redo of the restoration to please the patient anticipations.

One prior art method involved building a wax model of the proposed restoration and receive the recipient approval. The drawbacks of this method are: (I) The dentist usually can propose very limited options that are in the boundaries of his artistic capabilities expertise and cost; (ii) The method is a time consuming; (iii) The shade of the teeth are not included in this method, the wax do not demonstrate the shade of the porcelain; (iv) the success of this method depends on the technician's capabilities to copy the teeth structure that was approved by the recipient and the dentist.

However, also in this case, the preparation of the prosthesis, including the tinting of the prosthesis material, is performed at a dental laboratory and neither the recipient nor the dentist has any control on the final appearance of the prosthesis. Thus, also in this method of dental restoration, the recipient is often is not satisfied with the final appearance of the prosthesis.

A computerized manufacturing machine can be used to produce dental ceramic prosthesis or prosthesis core that provides strength and support to the overlying glass ceramic.

The glass ceramic can be applied to the computerized manufactured core by way of layering increments of wet powder (layering technique), when the prosthesis receives a general larger shape of the designated tooth it is to be sintered in a furnace achieving 700-1000 C to become a solid porcelain tooth.

The prosthesis can then be manually shaped (with burs on a rotary machine) to the obtain the final shape, then it is glazed with glass powder and sintered to receive a glossy finish. This technique requires high skills of the dental ceramists and requires long labor time (about 20-120 minutes per prosthesis unit).

Another possible way to overlay glass ceramic to the computerized (cad cam) manufactured core would be using lost wax or using digital cad cam grinded cavity tooth like shaped technique and then press technique. It is noted that this method has limitation, as the aesthetic is poor due to use of one shade porcelain. In order to improve aesthetics it is required to add translucent porcelain at the outer surface of the prosthesis using the layering technique and sinter this by a time consuming procedure. In addition the strength of the outer surface is reduced.

Another method is the making of single or more units when the cad cam machine makes the complete one or more crown.

These methods suffer from various drawbacks such as: (i) The production of the prosthesis is time consuming; (ii) the dental prosthesis is mono chromatic and as such, lacks the natural appearance aesthetic features, (iii) the core material is manufactured by costly computerized manufacturing centers, (iv) the cost of the manufacturing of a full shaped teeth is high due to the high cost of the milled blank ceramic block and the milling itself, and (v) a milling key adds more costs to the dentists and patient.

There is a growing need to improve the restoration process and especially to increase the predictability of the restoration process.

SUMMARY OF THE INVENTION

A method for preparing a dental prosthesis, the method includes: selecting a tooth matrix out of a group of tooth matrices that differ from each other, the tooth matrixes differs by at shape, size and/or shade, wherein each tooth matrix comprises an inner cavity; wherein the outer surface of the tooth matrix has an appearance of a tooth; and attaching at least a wall of the inner cavity of the tooth matrix to an intermediate element that is connected to the remaining tooth structure, core material or to the implant.

A method for preparing a dental prosthesis, the method comprising: selecting a tooth matrix out of a group of tooth matrices that differ from each other, wherein each tooth matrix comprises an inner cavity; wherein a tooth matrix has an appearance of a tooth; attaching at least a wall of the inner cavity of the tooth matrix to an intermediate element that is connected to the prosthesis core, remaining tooth structure or to the implant.

Conveniently, the method includes attaching the at least wall of the inner cavity by a bonding material that is selected based upon a desired color of the prosthesis.

Conveniently, the method includes illustrating to a patient an expected result of a restoration process by temporarily placing in a mouth of the patient a tooth replacement element that resembles a selected tooth matrix.

Conveniently, the method includes providing digital tooth matrix information to a computerized process that generates the intermediate element so that the intermediate element will be designed such as to fit in the inner cavity.

Conveniently, the method includes shaping the remaining tooth structure in response to a shape and size of an inner cavity of the selected tooth matrix, spacing porcelain and core structure and to a shape and a restoration area within the mouth of the patient.

Conveniently, the method includes shaping the remaining tooth structure in respect to a shape and size of a tooth grinding guide that is shaped so as to fit within the inner cavity of a tooth matrix, the space of the bonding element and core material width.

Conveniently, the method includes selecting a light transparent tooth matrix and a color of an adhesive that bonds the tooth matrix to the element.

Conveniently, the method includes determining a relative gap between a selected tooth matrix and an intermediate element, and associating a gap filling material with the tooth matrix.

Conveniently, the method includes sintering the gap filling material.

Conveniently, the method includes generating the tooth matrix.

Conveniently, the method includes generating a multi-layered tooth matrix.

Conveniently the method includes taking an impression for an index.

Conveniently the method includes making an index to secure relative position between the prosthetic core and tooth matrix.

A method for generating a tooth matrix, the method includes: determining a shape of a tooth matrix out of a group of tooth matrices that comprises multiple tooth matrices that differ from each other, wherein each tooth matrix comprises an inner cavity; wherein a tooth matrix has an appearance of a tooth; and manufacturing, in response to the determination, the tooth matrix; wherein the inner cavity is shaped so as to include an intermediate element that is connected to a remaining tooth structure or an implant.

Conveniently, the method includes manufacturing a tooth matrix that comprises multiple layers, wherein an outer layer is light transparent.

Conveniently, the method includes applying a manufacturing process selected from a group consisting of: cold pressing, cold isostatic pressing, melt drawing, injection molding, hot pressing, extrusion processing, die pressing, slip casting, extrusion, injection molding, tape casting, green machining and sintering.

Conveniently, the method includes manufacturing multiple layers of the teeth matrix by and molding the multiple layers to form a teeth matrix.

Conveniently, the method includes manufacturing multiple layers of the teeth matrix that differ from each other by a level of light transmission.

Conveniently the inner cavity is shaped to include the core and wherein a space for fill-in material is formed between the inner cavity and the core.

A method for generating a core, the method includes: receiving tooth matrix digital information and restoration area information; and applying a computerized process to design and manufacture the core so that the core substantially fits to a gap between an inner cavity of the tooth matrix and a remaining tooth structure or an implant located in the restoration area.

Conveniently, the method includes generating a multi-layered tooth matrix.

A tooth matrix, that includes: an outer surface, that resembles an outer surface of a tooth; an intermediate portion that is at least partially light transmissive; wherein the intermediate portion defines an inner cavity that is shaped such as to fit an intermediate element that is connected to a remaining tooth structure or to an implant.

Conveniently, the tooth matrix includes a light transmissive outer surface; and wherein the intermediate portion comprises multiple layers that differ from each other by their transmission level.

Conveniently, the tooth matrix includes an enamel layer, a dentine layer, an enamel junction dentin layer and a pulp matter layer.

A kit, that includes: a group of teeth matrices that differ from each other, each tooth matrix includes an inner cavity; wherein a tooth matrix has an appearance of a tooth; and tooth grinding guides; wherein the outer shape has the appearance of the corresponding tooth matrix outer surface and the inner surface has the appearance of the final tooth or implant preparation. The distance from the tooth grinding outer shape to its inner shape includes space for: the width of the core material, the width of the fill in material and the width of the tooth matrix.

Conveniently, an inner cavity of a tooth grinding guide is smaller than the inner cavity of the teeth matrix and wherein a gap between the upper portion of the tooth grinding guide and a inner space is large enough to include binding material core material.

Conveniently the kit includes temporary teeth, each temporary teeth having an outer surface that is substantially equal to an outer surface of teeth matrix and has an inner cavity that is larger than a teeth structure to which the temporary teeth should be connected to.

Conveniently the kit includes measurement equipment for measuring the restoration area.

BRIEF DESCRIPTION OF THE DRAWINGS

The foregoing and other objects, features, and advantages of the present invention will become more apparent from the following detailed description when taken in conjunction with the accompanying drawings. In the drawings, similar reference characters denote similar elements throughout the different views, in which:

FIG. 10 illustrates a method according to an embodiment of the invention;

DETAILED DESCRIPTION OF THE DRAWINGS

Conveniently, the predictability of restoration process is increased by utilizing tooth matrices that have a known shape.

In a sense the restoration process begins by defining the external shape (selecting a tooth matrix out of multiple prefabricated tooth matrices) of the prosthesis and ends by binding a tooth matrix to a core or other intermediate element.

It is noted that multiple teeth can be reconstructed using the suggested method. Any tooth can be reconstructed.

Conveniently, a tooth matrix (also referred to as prefabricated tooth matrix) is provided. It is an element that includes an outer surface, that resembles an outer surface of a tooth and an intermediate portion that is at least partially light transmissive. The intermediate portion defines an inner cavity that is shaped such as to fit an intermediate element that is connected to a remaining tooth structure or to an implant.

Multiple tooth matrices are provided to a dentist and/or to a dental laboratory. They can differ from each other by shape, size and even color. There are shaped and sized in order to replace different teeth (for example—incisor, bicuspid premolar, canine, molar, and the like upper and/or lower jaws) of different patients. The patients can differ by the size of their tooth, the shape of their face and other parameters.

Conveniently, the different tooth matrices are designed in order to provide an adequate solution for most of the population, selected parts of the population or all the population.

Conveniently, the tooth matrix resembles the tooth it replaces. It can include a light transmissive outer surface and the intermediate portion.

The intermediate portion can include multiple layers that differ from each other by their transmission level.

Conveniently, the tooth matrix can include an enamel layer, a dentino enamel junction layer, a dentin layer and a pulp matter layer. Between layers and/or within layers can include reinforcing material to increase strength and/or dye material to improve the aesthetic of the restoration.

A kit is provided, it include: a group of teeth matrices that differ from each other, each tooth matrix comprises an inner cavity; wherein a tooth matrix is has an appearance of a tooth; and tooth grinding guides; wherein an upper surface (portion) of a tooth grinding guide is shaped according to an inner cavity of a corresponding tooth matrix.

The upper portion of a tooth grinding guide is smaller than the inner cavity of the teeth matrix and a gap between the upper portion of the tooth grinding guide and a inner space is large enough to include binding material, and optionally core material.

The kit can include temporary teeth, each temporary tooth having an outer surface that is substantially equal to an outer surface of teeth matrix and has an inner cavity that is larger than a remaining teeth structure.

The kit can include measurement equipment for measuring the restoration area to facilitate selection of the tooth matrixes.

Figure 8:
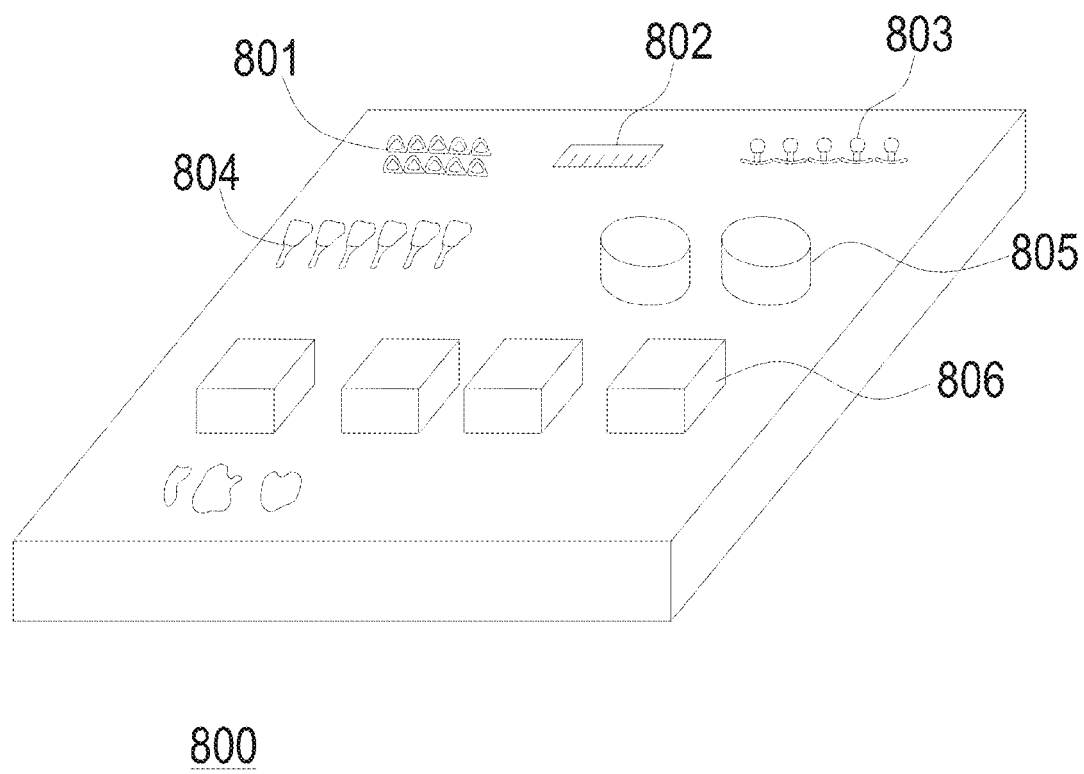
FIG. 8 illustrates a kit according to an embodiment of the invention.

FIG. 8 illustrates a sample of such a kit.

Figure 1:
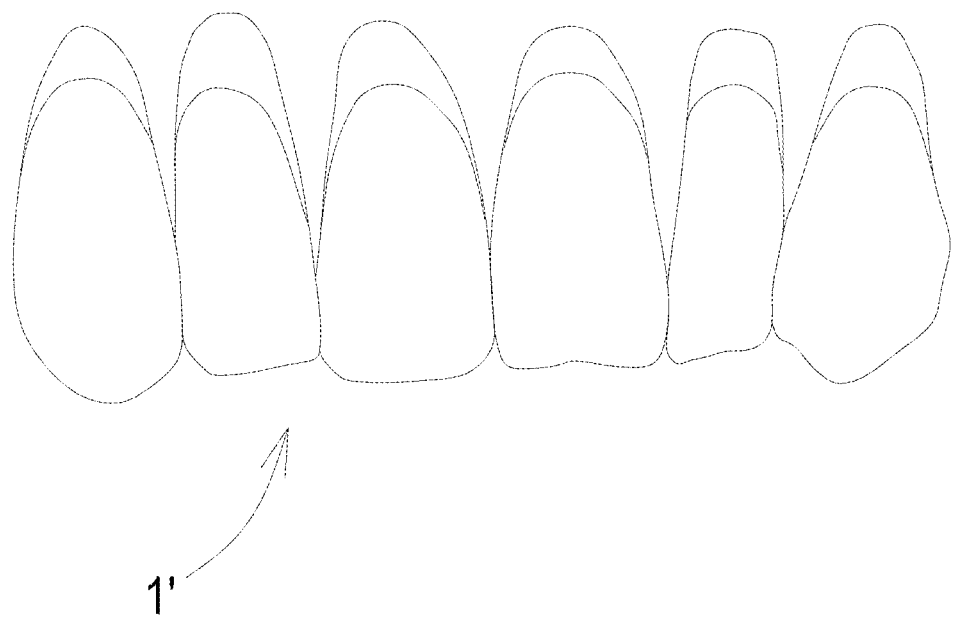
FIG. 1 illustrates various shapes of a tooth that resemble tooth matrices, according to an embodiment of the invention.

FIG. 1 provides non-limiting examples of the shapes (collectively denoted) 1' of tooth.

Figure 1A:
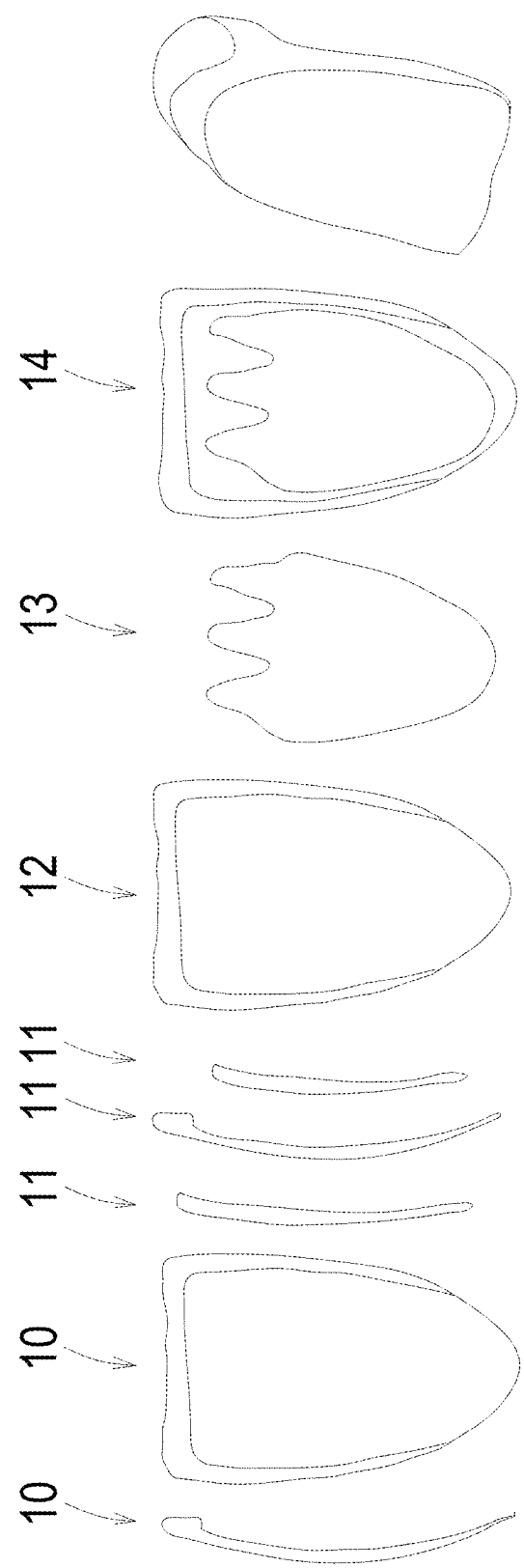
FIG. 1A represent the different shapes of various the tooth matrixes according to an embodiment of the invention.

FIG. 1A provides various views of various the tooth matrixes according to an embodiment of the invention. Side views of various tooth matrices are denoted 10 and 11 while front views of various tooth matrices are denoted 10, 12, 13 and 14.

Figure 2C:
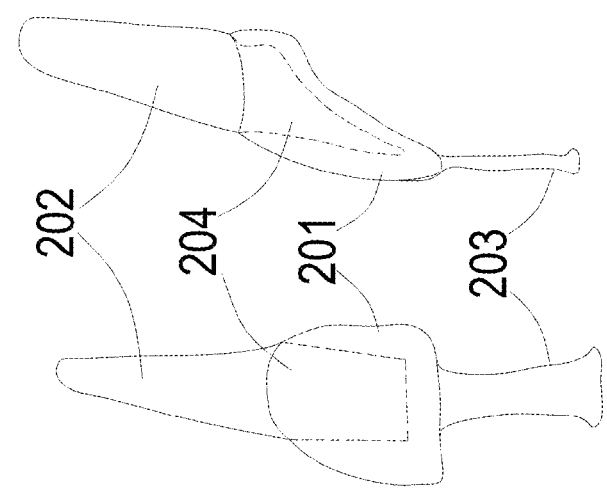
FIGS. 2A-2C illustrate a tooth root, grinding guides and a handle according to an embodiment of the invention.
Figure 2B:
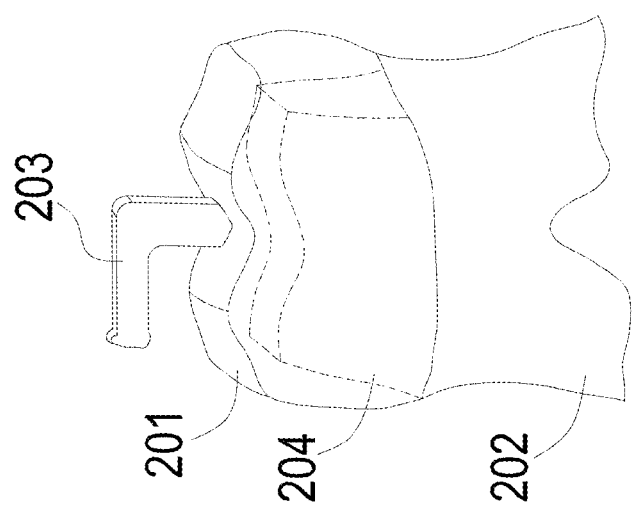
Figure 2A:
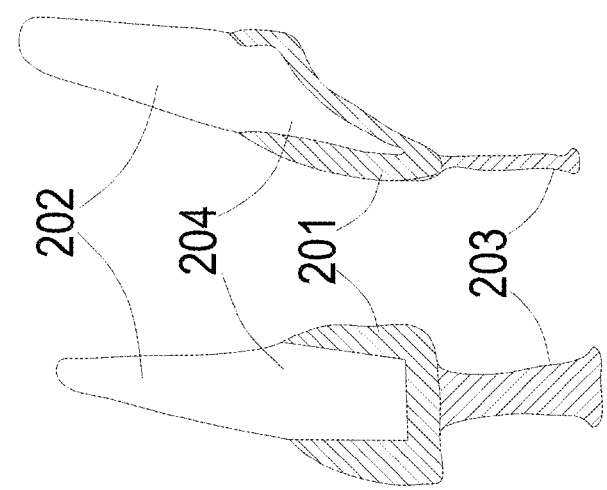
Figure 3A:
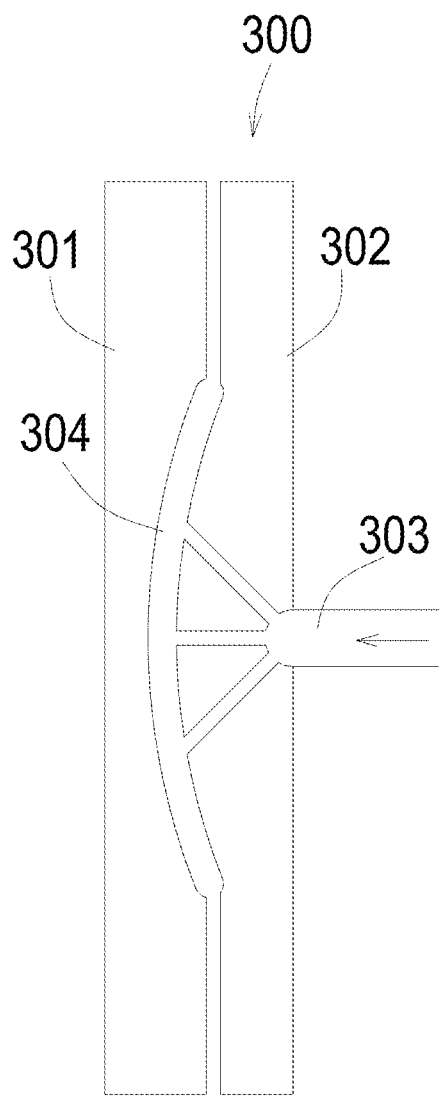
FIGS. 3a-3b illustrate by way of example only a cast used for multi layer during a molding process of a tooth matrix, according to an embodiment of the invention.
Figure 3B:
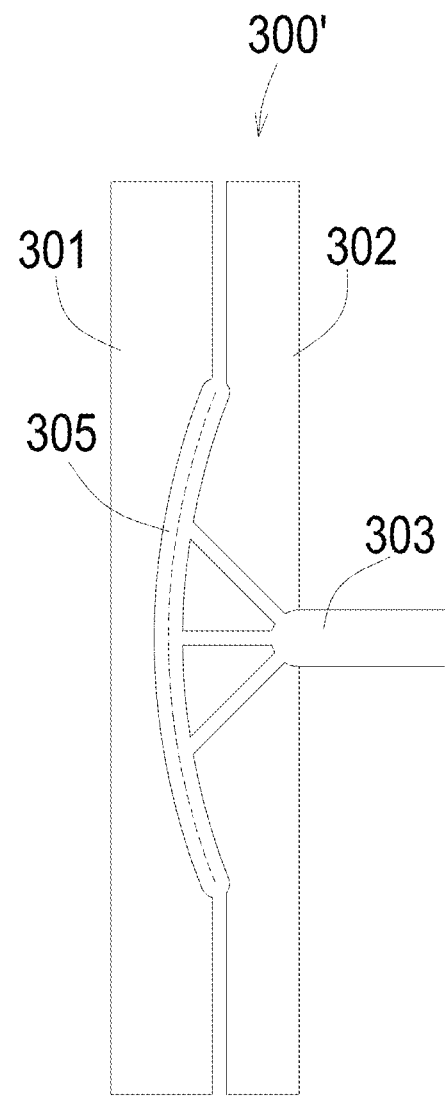
Figure 4:
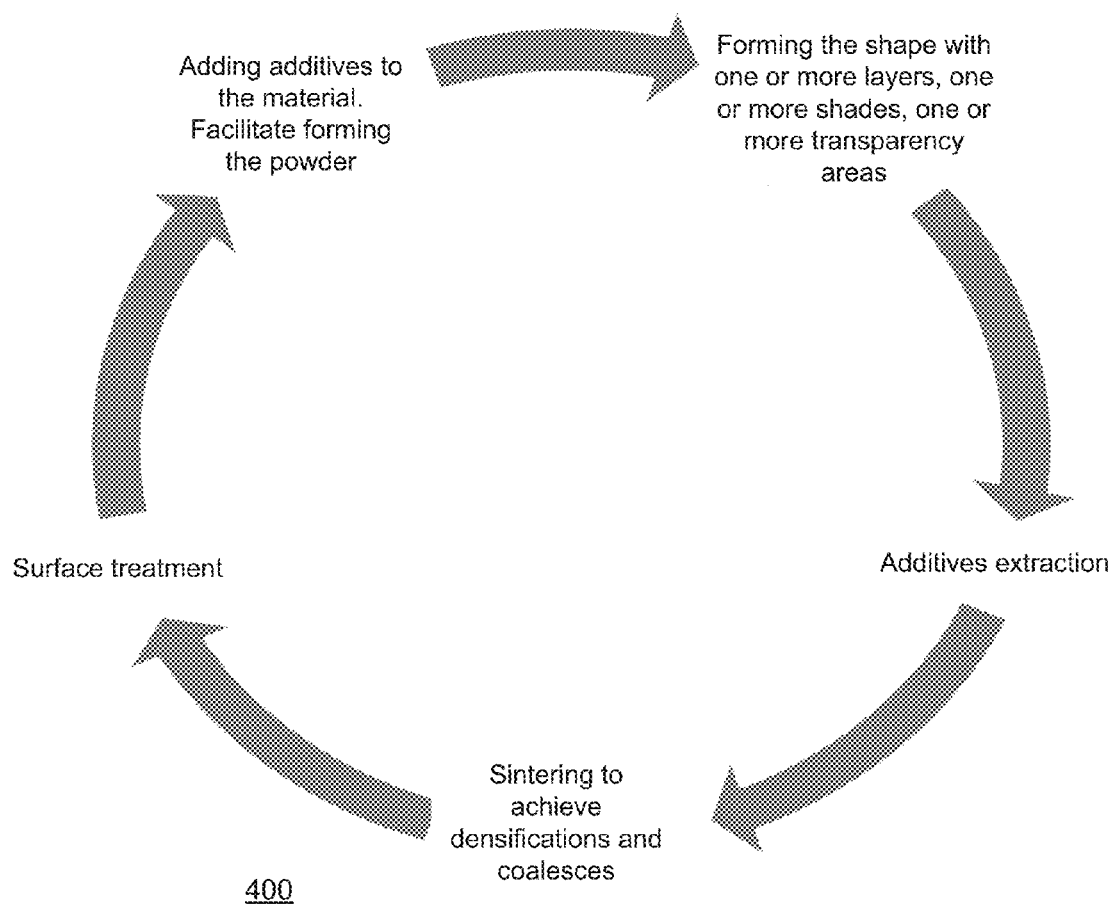
FIG. 4 illustrates various stages of a sequence for generating a tooth matrix according to an embodiment of the invention.

FIGS. 2A-2C illustrate a tooth root 202, transparent grinding guides 201, handle 203 and prepared (treated) tooth 204, according to an embodiment of the invention;

FIGS. 3a-3b illustrate by way of example only casts 300 and 300' used for multi layer during a molding process of a tooth matrix, according to an embodiment of the invention. Each of casts 300 and 300' includes two portions 301 and 302 that define a space 304 that can be filled by filling material that is injected via inlet 303. One portion (such as 302) can be a movable portion.

Figure 5:
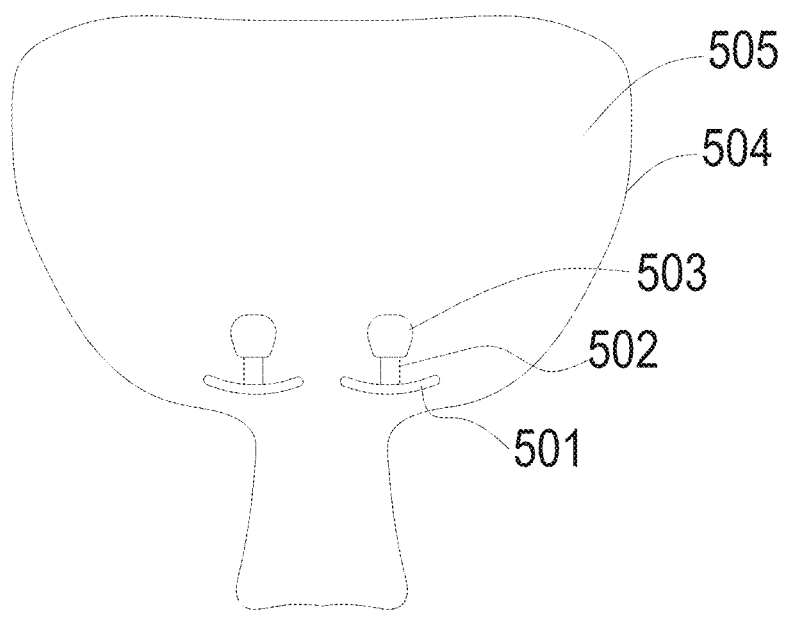
FIG. 5 illustrates a tooth, enamel veneers matrixes, adhesive material that connects the tooth matrixes and prepared tooth, a tray and impression material according to an embodiment of the invention.

FIG. 5 illustrates a tooth matrix 501, adhesive material 502, prepared tooth covered with core material 503 and impression tray 504.

Figure 6:
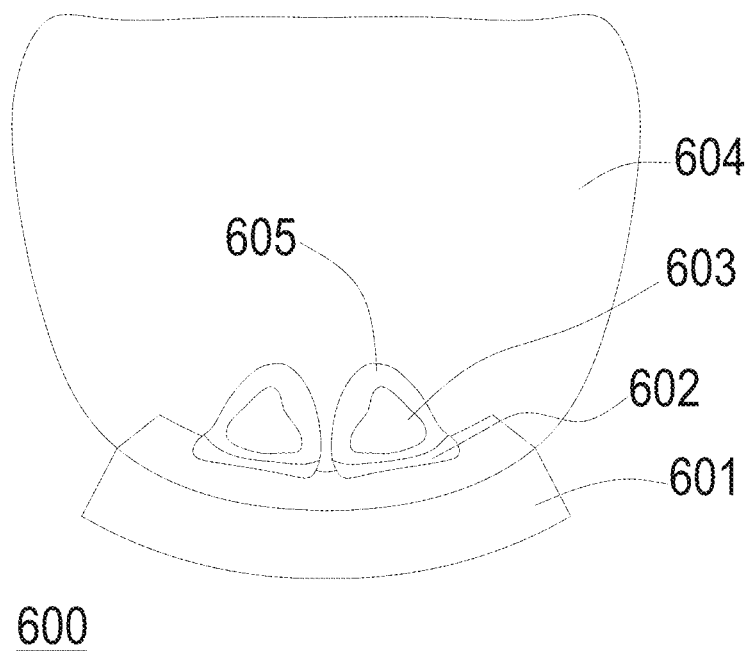
FIG. 6 illustrates a tooth, enamel veneers matrixes, adhesive material that connects the tooth matrixes and prepared tooth, a tray and impression material according to an embodiment of the invention.
Figure 7:
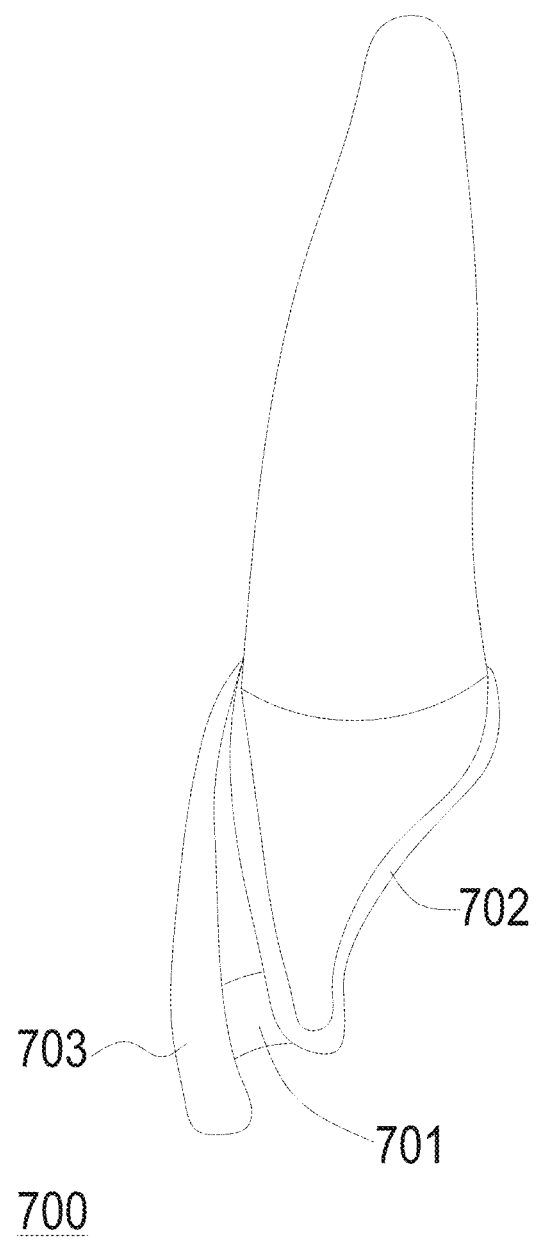
FIG. 7 illustrates an adhesive material, a core and an tooth matrix according to an embodiment of the invention.

The adhesive material 502 connects the tooth matrixes 501 and prepared tooth, a tray and impression material according to an embodiment of the invention;

FIG. 6 illustrates a tooth, enamel veneers matrixes, adhesive material that connects the tooth matrixes and prepared tooth, a tray and impression material according to an embodiment of the invention;

FIG. 7 illustrates adhesive material 701, a core 702 and an tooth matrix 703 according to an embodiment of the invention.

FIG. 8 illustrates a kit 800 according to an embodiment of the invention. Kit 800 includes multiple tooth matrices 801, a ruler 802 for measuring the size of the teeth, a temporary teeth form with adhesive 803, a tooth grinding guide 804, adhesive 805, ceramic 806 for lab and a shade guide 807.

The tooth matrix can be selected by the mentioned below process.

Once the patient (recipient) needs to replace a one or more tooth with dental prosthesis, a sequence of stages can be followed in order to insure that an exact form and shade of teeth are provided.

These stages can start by a diagnostic stage—at this stage the dentist offers and suggest to the patient, and with the patient, the general form, shape size and shade of the restoration final result.

The diagnostic stage can include one of the following stages or a combination thereof:

(a) The dentist can choose from a variety of Teeth Like shapes (denoted 1' in FIG. 1) form design and shade on a catalog and instruction in the kit (FIG. 8) or computer files. The preferred form of teeth will be in harmony with the outer shape of the patient dentition, face and appearance. It is known to the art four different categories of face-teeth harmonies forms; rectangular, triangular, oval, and round.

(b) In the shape category there are different shapes of Teeth Like (FIG. 1) between vigorous and soft teeth appearance depending on the patient gender, personality and appearance.

(c) The dentist then chooses the shade of the restoration from a range of bright to dark teeth according to the related (adjacent) teeth and the patient preferences. The shades will be chosen with the aid of shade guide in the kit (FIG. 8).

(d) The dentist measures the accumulate size of the adjacent teeth to be restored from mesial to distal, and/or the separate size of each tooth with the aid of a ruler (FIG. 8). The dentist also measures the length of the teeth from the cervical aspect of the one or more teeth to the incisal edge of the one or more teeth, this measurement is made also according to what known to the art, like lip line, ocullusal limitations of the restoration and the well-known to the art of matching the teeth location and size in harmony of the persons appearance-smile-design rules for matching to patient appearance and teeth.

The diagnostic stage can be done with "Face recognition" program (e) When the information of all the above mentioned steps acquired, the dentist can pick the right Teeth Like Adhesive (FIG. 8—element c) of veneers that are able to be located in the patient mouth. The veneers contain the final shape; shade and position of the proposed prosthetic. The adhesive veneer teeth are placed it in the patient's mouth for demonstration of how the restoration will look like when completed. Once received the patient approval to the particular tooth matrix set (FIG. 1, 8) a series of action and components that are design to serve for the purpose of consistent predictability. The Restoration set guides the labor to achieve it. The dentist and patient now have mutual knowledge how the restoration will look like and what to aim for in the next stages of the restoration construction.

After the diagnostic stage is completed a tooth/teeth physical and or digital impression of the restoration and neighboring working area (FIG. 5) is sent to a dental laboratory.

In order to obtain the impressions for the lab the dentist has to go through several steps (also referred to as dentist tooth preparation stages):

a. The final result has been set in the diagnostic and patient approval stage, the size of the teeth comprising the restoration and their position in the mouth is known and approved by the patient, as a result it is also known the amount of tooth reduction that should be made to make space for the aesthetic buildup of the core structure and the porcelain.

b. The kit (FIG. 8) provides for the one or more teeth preparation a Tooth Grinding Guide (FIG. 2a-c). The Tooth Grinding Guide is transparent matrixes that have the outer shape of the tooth (similar to the outer surface of the Tooth Matrix, the inner shape that can be seen from the outside of the matrix resembles the size and structure of optimal prepared tooth for the design chosen in the previous stage. It is advised that every tooth will have a corresponded matrix. The purpose of the preparation matrix is to provide a guided tooth preparation in respect of optimal tooth size reduction to allow the buildup components for the final result. The tooth preparation matrix will be called in this paper Tooth Grinding Guide (FIG. 2, 8d.)

c. The preparation sequence will follow the described steps: general reduction, placing the Tooth Grinding Guide (FIG. 2) until it is fully sited on the prepared tooth. Careful attention should be drawn to the outer surface of the matrix since this surface will represents the position of the final restoration.

d. Once the dentist starts to grind the tooth using the Tooth Grinding Guide (FIG. 2) he will be guided to set the correct amount of grinding from every site of the tooth, in a way of example only, a protruded tooth which is designed to be in its normal position, by using Tooth Grinding Guide (FIG. 2) will direct the dentist to grind more from the occlusal incisel and bucal or labial sides and less from the palatal side, this is done by showing the dentist the final size and position of the tooth from the outer side of the Tooth Grinding Guide (FIG. 2) which resembles a tooth shape and from its inner side cavity that marks the size and shape of the prepared tooth.

e. Once the teeth has been prepared according to the guidance of the Tooth Grinding Guide two possible options are: a. impression, known to the art, of the prepared teeth is being taken using a digital or plastoelasto material, the impression material is in fully plastic stage and after the impression is inserted the material is set to a fully elastic stage, b. optional procedure will include the Enamel matrixes in the impression stage: The veneers or Tooth matrix (FIG. 1) is placed on the prepared teeth they located to the desired position and temporarily secured (FIG. 7) to the prepared teeth and impression is taken. This will provide the dental technician with the relative position between the prepared teeth and the location and size of the final restoration.

The dental laboratory receives the impression and pour cast stone to receive the positive structure of the imprinted mouth. The lab then constructs from a selection of materials known to the art the core structure and sends it to the dentist for try on to assure fitness of the core to the teeth.

In case option b is selected then the dental laboratory worker can make an index (FIG. 6) of the position relation between the Tooth matrix and the prepared teeth.

The dentist can receive from the dental laboratory the core and place the core on the prepared teeth. If there is a good enough fit between the chosen Tooth matrix set and the core then the tooth matrix is placed on the core using a light sensitive adhesive (FIG. 7). The patient approves the setup and an impression is taken for the lab.

This stage is followed by a dental laboratory final preparation stage. During this stage the dental technician makes an index of the relative position between the core and the tooth matrix (FIG. 6A) as designed by the dentist with the approval of the patient. The index serves for positioning the Tooth matrix while the porcelain slurry (made of liquid and powder porcelain) is poured between the core and the Tooth matrix (FIG. 6E). When the excess of the liquid is drained from the slurry the index is removed and the new structure (FIG. 6B,E) is being sintered in temperature that is lower than the Tooth matrix production sintering temperature.

At this stage particular demands like special tooth shade effects and structural effects like different component inserts can be made to enhance and individualize the prosthesis.

According to another embodiment of the invention the dentist can use the tooth matrix system to obtain an immediate aesthetic makeover.

The dentist can employ stages a-e of the diagnostic stage, stage a-d of the dentist tooth preparation stages, and then have an approved set of teeth matrixes which answer patient aesthetic and functional anticipations (steps a-e of the diagnostic stage).

The dentist should use composite material or other means that are known to the art to lute and secure the selected teeth in their corresponded preparations.

Following all or part of the procedures described above will secure a method that enable the dentist and patient to visualize and determent the final result at the beginning of the process, this method will insure the Prosthesis predictability.

Conveniently, the Tooth matrix can be applied to computer aided design (CAD) processes that manufacture cores. Computer automated equipment can fabricate a one or more core material from metals like titanium for implants and aesthetically oriented like Aluminas and zirconiums. This is frequently referred to as digital dentistry, where computer automation is combined with optics, digitizing equipment, CAD/CAM (computer-aided design/computer aided machining) and mechanical milling tools. Examples of such a computer-aided milling machine include the CEREC 2™ machine supplied by Siemens (available from Sirona Dental Systems; Bensheim, Germany); VITA CELAY™ (available from Vita Zahnfabrik; Bad Säckingen, Germany); PRO-CAMT' (Intra-Tech Dental Products, Dallas, Tex.); and PROCERA ALLCERAM™ (available from Nobel Biocare USA, Inc.; Westmont, Ill.). U.S. Pat. Nos. 4,837,732 and 4,575,805 also disclose the technology of computer-aided milling machines for making dental prostheses.

The tooth matrix when it has fewer walls and/or path of insertion can be used for the following stages.

The digital computer files that describe the inner shape of the Tooth matrix can be integrated into the Cad-Cam core designing files, so that they leave optimal space for adaptation with the inner surface of the Tooth matrix.

A typical space will be 0.1 mm-2.5 mm. This space will be filled with the appropriate glass ceramic to adjust thermal coefficient and strength. The Tooth matrix will be filled with the slurry porcelain and secure to the bad on the core material. Another possible application is filling the space between the core and the tooth matrix with cold lutting like dental light cured composites material that can be set without the aid of a laboratory machining by the dental technician and also to be managed chair side.

This feature can facilitate more the labor of the dental technician; he will have to fill-in just the exact glass ceramic powder slurry, as a result there would be less build up that would save a substantial amount of time laboring material saving and reduced costs.

The tooth matrix can be manufactured by applying one or more methods of making dental tooth matrix (Enamel Shell) such as but not limited to: cold pressing, melt drawing, injection mold, hot pressing and extrusion processes, die pressing, slip casting and extrusion, injection molding and tape casting. Hot pressing, hot isostatic pressing, cold isostatic pressure, and pressure casting. With the aid of additives or without.

Sintering for processing ceramic of the tooth matrix (Enamel Shell) is performed, it is preferred that the material be fully sintered to achieve greater than about 98% of the theoretical density of the ceramic material. More preferably, fully sintering achieves greater than about 99.0% theoretical density, and most preferably greater than 99.5% of the theoretical density. The Tooth matrix (Enamel Shell) can be fabricated by pressing powder to a desired shape and sintering the pressed compact at temperatures close enough to the material's melting point so that the ceramic coalesces and densifies. In one such manufacturing technique, high purity aluminum oxide powder is placed in the die cavity of a high-pressure press. Submicron size particles can be used. Hot pressing accelerates the sintering process and allows one to achieve substantially greater density in the sintered compact. Methods that are known to the art like powder injection molding may also utilize to produce the tooth matrix.

The Tooth matrix may be provided at near full density (>95% of theoretical).

Alternatively, it may be provided with sufficient porosity partially sintered as to facilitate machining and final sintering with the fill-porcelain. Theoretical density for a crystalline ceramic is calculated from the atomic weights of the constituents and the volume of the crystallographic unit cell.

If desired, the inventive Tooth matrix can be hot isostatic pressed (HIP) to accelerate the sintering process. In a press, isostatic pressure is applied while the material is heated to the sintering temperature. The combination of high temperature and high pressure compact the HIPed part to have substantially zero porosity. U.S. Pat. No. 4,954,080 provides further discussion as to hot isostatic pressing aluminum oxide, the disclosure of which is incorporated by reference.

Yet another method for producing a rod of crystalline ceramic material is described in U.S. Pat. No. 4,639,218, which refers to an EFG (Edge-defined, Film-fed, Growth) modification of the Czochralski process for growing crystalline alpha-alumina. Alternatively, hot forging of ceramic can be employed to form the tooth matrix.

Tooth matrix ceramic powder is mixed with a viscous material to enable the powder flow to form a designed shape of a tooth. The powder mix includes of a fine ceramic powder with the appropriate additions of binder(s) and plasticiser(s) to give the desired flow properties (rheology), either cold or when heated prior to being forced through the die. filling of a mould, a negative of the Tooth matrix, a plastic mix is prepared and heated in the barrel of the molding machine until it is at the correct temperature at which the mix has a sufficiently low viscosity to allow flow if pressure is applied to form the Tooth matrix by low to high pressure.

A plunger is pressed against the heated mixture forcing it through an orifice and on into the Tooth matrix tool cavity. The molded Tooth matrix is removed from the die and the organic binder is slowly burnt out in a controlled atmosphere by means of a carefully controlled heating schedule, prior to sintering.

The mentioned above phase of manufacturing is illustrated in FIGS. 2A-2B.

The Tooth matrix can be manufacturing with one or more layers. The outer layer would be preferably from clear transparent material designed to represent the enamel of a natural tooth, the clear layer preferably will vary in width from 0.2 mm to 1.2 mm. The use of a light transmissive material for a Tooth matrix allows internal tailoring of the appearance of the restoration by modifying both the color of the ceramic slurry in the dental laboratory, or by lutting or bonding agent for immediate aesthetic makeover by the dentist.

In case of the production of more then one layer, the production will include more stages. The second layer from enamel powder will employ certain areas of the Tooth matrix to provide shade of natural tooth. The third layer will include dentin ceramic material to provide more shade to the Tooth matrix. On the cervical aspect of the Tooth matrix a darker material preferably is added. In multiple layers, depends on the manufacturing technique chosen on or more stages are employed. In a way of example only, in molding, the part of the mould that configure the inner part of the Tooth matrix will be replaced with a hemi-mould part that will provide space for a second layer to be added to the Tooth matrix cavity in all manufacturing procedures. By way of example only in press procedure different powders are employed to regulate the layers in the designed order to achieve aesthetic pleasing and natural Tooth matrix.

Alternate way for the added layers to Tooth matrix would be by means of separate molding procedure for each layer as described above. The separate layers that will be finely adjusted in terms of shape, color, thermal coefficient expansion, and other thermal properties that are needed for combined sintering.

The layers will be added together to comply a form of a Tooth matrix and will be sintered together to become one piece of Tooth matrix.

The surface treatment of the Tooth matrix can be in the range of: as sintered to 1N in the scale of New ISO scale numbers for the outer surface of the Tooth matrix. The higher scales of surface finish from as sintered will be achieved by machine polishing.

The inner portion of the Tooth matrix can be designed to be rough as possible in the range from as sintered to etched by means that are known to the art.

Green machining can also be applied. This technique can be applied to as-pressed of the tooth matrix which is still in a chalky condition. Common metal working machines are used to machine the Tooth matrix for individual appearance in this soft condition as greater material removal rates are possible than by post sintering.

Tolerance of the teeth matrix can be about 0.05 to 0.2 mm.

Once the Tooth matrix ceramic powder has been compacted and green machined (if required) the powder compact. Densification is achieved by sintering at temperatures up to 1800° C.

The sintering or firing process provides the energy to encourage the individual powder particles to bond or sinter together to remove the porosity present from the compaction stages.

During the sintering process the green compact shrinks. However, this shrinkage is predictable and can be accommodated.

Hot Pressing can be applied during the manufacturing process. It can include simultaneous application of external pressure and temperature to enhance the tooth matrix densification. It is conducted by placing either tooth matrix powder or a compacted perform into a suitable die, typically graphite, and applying uni-axial pressure while the entire system is held at an elevated temperature, up to 2000° C.

Hot Isostatic Pressing can be applied during the manufacturing process. The Tooth matrix hot isostatic pressing casting technique involves sintering a compact at high temperature in a pressurized gas atmosphere. The compact must either be impermeable to the pressurizing gas or be encapsulated in a gas-tight container. Hot Pressing is especially suited to relatively simple shapes, with the components usually requiring diamond grinding to achieve the finished tolerances In the former case, powder compacts are first sintered to remove surface connected porosity.

The use of hot isostatic pressing leads to additional densification and increased strength.

The teeth matrix can be made of various materials such as dental glass ceramic is in correlation of thermal expansion coefficient with the core material.

Material orientation: the material to be used with physical properties to comply with such core material that are known to the art of making dental porcelain restoration i.e.; metals Aluminas Zirconiums Teeth matrices of various shapes, color and size can be provided. These different shapes can be provided to a dentist to be selected of. They can be represented in a catalog or in computer files.

The tooth matrix can also serve to build a coreless crown (a dental prosthesis without a core) or bridge, the tooth matrix when achieve strength greater then 250 Mpa can support the occlusal forces, therefore the prosthesis does not need internal reinforcement of a core. The coreless tooth matrix when it is made from pure transparent alumina will include voids in the oclusal area to be filled with material which will match the hardness of the natural enamel. The following steps will be taken to make the coreless prosthesis. A. selection of the appropriate tooth matrix. B. isolating the tooth stamp (chairside) or the representation tooth stamp from the stone cast (dental laboratory). C. filling the gap with light cure composite (chairside), or porcelain and sintering (dental laboratory).

The tooth matrix includes one or more layers and at least one layer can be made of light transmissive material to provide aesthetically pleasing dental prostheses.

The outer structural appearance of a tooth matrix can resembles of the outer surface of a tooth.

The inner surface of the tooth matrix is rough and can include undercuts.

The tooth matrix can include one or more layers of different light transmission properties.

The tooth matrix can include the layers generally will be arranged as resembles a natural tooth layers e.g. Enamel, dentino enamel junction dentin and pulp matter.

The layers can be modified to achieve aesthetic results

The Tooth matrix will be produced by method and process which are known to the art for handling production of powder and molted ceramic material, The tooth matrix can be produce from a layer which will be clear (transparent) of color and receive the color from the layer under the inner surface of the matrix.

Figure 9:
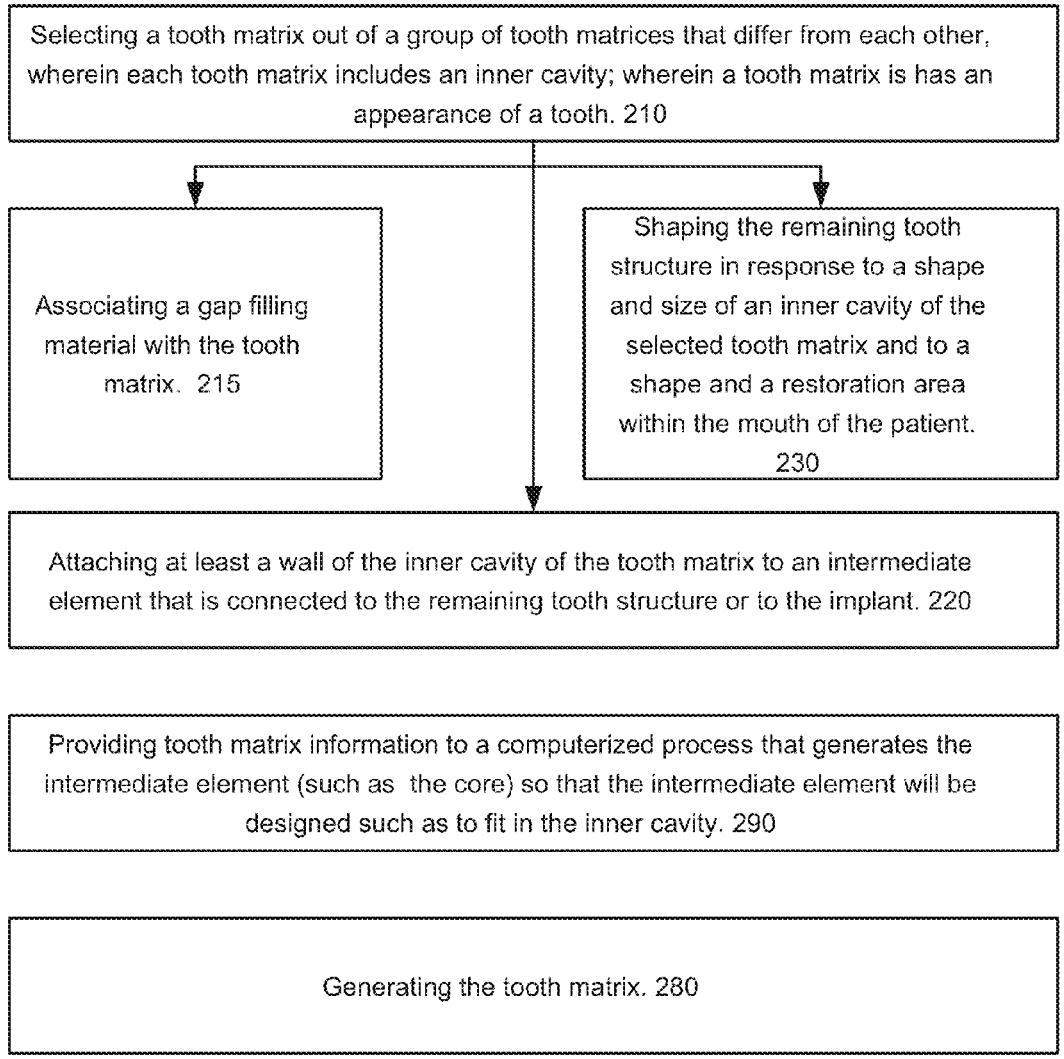
FIG. 9 illustrates a method according to an embodiment of the invention.

FIG. 9 illustrates method 200 for preparing a dental prosthesis, according to an embodiment of the invention.

Method 200 starts by stage 210 of selecting a tooth matrix out of a group of tooth matrices that differ from each other, wherein each tooth matrix includes an inner cavity; wherein a tooth matrix is has an appearance of a tooth. Stage 210 can include selecting between tooth matrices that differ by their size, shape, color. It is noted that the color can be determined by the color of adhesive material and/or fill-in (porcelain) that connects the tooth matrix to the intermediate element—especially when the tooth matrix is transparent or partially transparent.

Stage 210 can include illustrating to a patient an expected result of a restoration process by temporarily placing in a mouth of the patient a tooth replacement element that resembles a selected tooth matrix. This tooth replacement element can be a temporary element.

Stage 210 can include selecting a light transparent tooth matrix and a color of an adhesive that bonds the tooth matrix to the element.

Stage 210 can include determining a relative gap between a selected tooth matrix and an intermediate element.

Stage 210 can be followed by stage 215 of associating a gap filling material with the tooth matrix. Stage 215 is followed by stage 220.

Stage 215 can include sintering the gap filling material.

Stage 210 is followed by stage 220 of attaching at least a wall of the inner cavity of the tooth matrix to an intermediate element that is connected to the remaining tooth structure or to the implant.

Stage 220 can include attaching the at least wall of the inner cavity by a bonding material that is selected based upon a desired color of the prosthesis.

Stage 210 can also be followed by stage 230 of shaping the remaining tooth structure in response to a shape and size of an inner cavity of the selected tooth matrix and to a shape and a restoration area within the mouth of the patient.

Stage 230 can include shaping the remaining tooth structure in response to a shape and size of an tooth grinding guide that is shaped so as to fit within the inner cavity of a tooth matrix.

Stage 230 is followed by stage 220.

Method 200 can also include stage 290 of providing tooth matrix information to a computerized process that generates the intermediate element (such as the core) so that the intermediate element will be designed such as to fit in the inner cavity.

Method 200 can also includes stage 280 of generating the tooth matrix. Stage 280 includes generating a multi-layered tooth matrix. It can include any stage of method 300 or a combination thereof.

FIG. 10 illustrates method 300 for preparing a dental prosthesis, according to an embodiment of the invention.

Method 300 starts by stage 310 of determining a shape of a tooth matrix out of a group of tooth matrices that includes multiple tooth matrices that differ from each other, wherein each tooth matrix comprises an inner cavity; wherein a tooth matrix has an appearance of a tooth. Wherein the inner cavity is shaped so as to include an intermediate element that is connected to a remaining tooth structure or an implant.

Stage 310 is followed by stage 320 of manufacturing, in response to the determination, the tooth matrix.

Stage 320 can include manufacturing a tooth matrix that comprises multiple layers, wherein an outer layer is light transparent.

Stage 320 can include applying at least one manufacturing process out of: pressing, melt drawing, injection molding, hot pressing, extrusion processing, die pressing, slip casting, extrusion, injection molding, tape casting, green machining, and sintering.

Stage 320 can include manufacturing multiple layers of the teeth matrix by molding the multiple layers to form a teeth matrix.

Stage 320 can include manufacturing multiple layers of the teeth that differ from each other by a level of light transmission.

Figure 11:
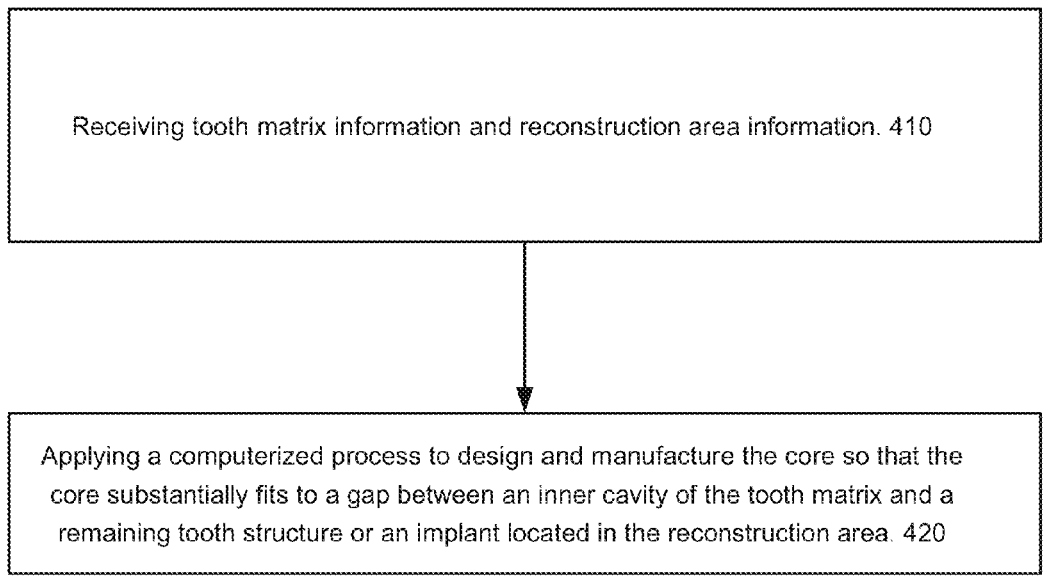
FIG. 11 illustrates a method according to an embodiment of the invention.

FIG. 11 illustrates method 400 for preparing a dental prosthesis, according to an embodiment of the invention.

Method 400 starts by stage 410 of receiving tooth matrix information and restoration area information.

Stage 410 is followed by stage 420 of applying a computerized process to design and manufacture the core so that the core substantially fits to a gap between an inner cavity of the tooth matrix and a remaining tooth structure or an implant located in the restoration area.

Figure 12:
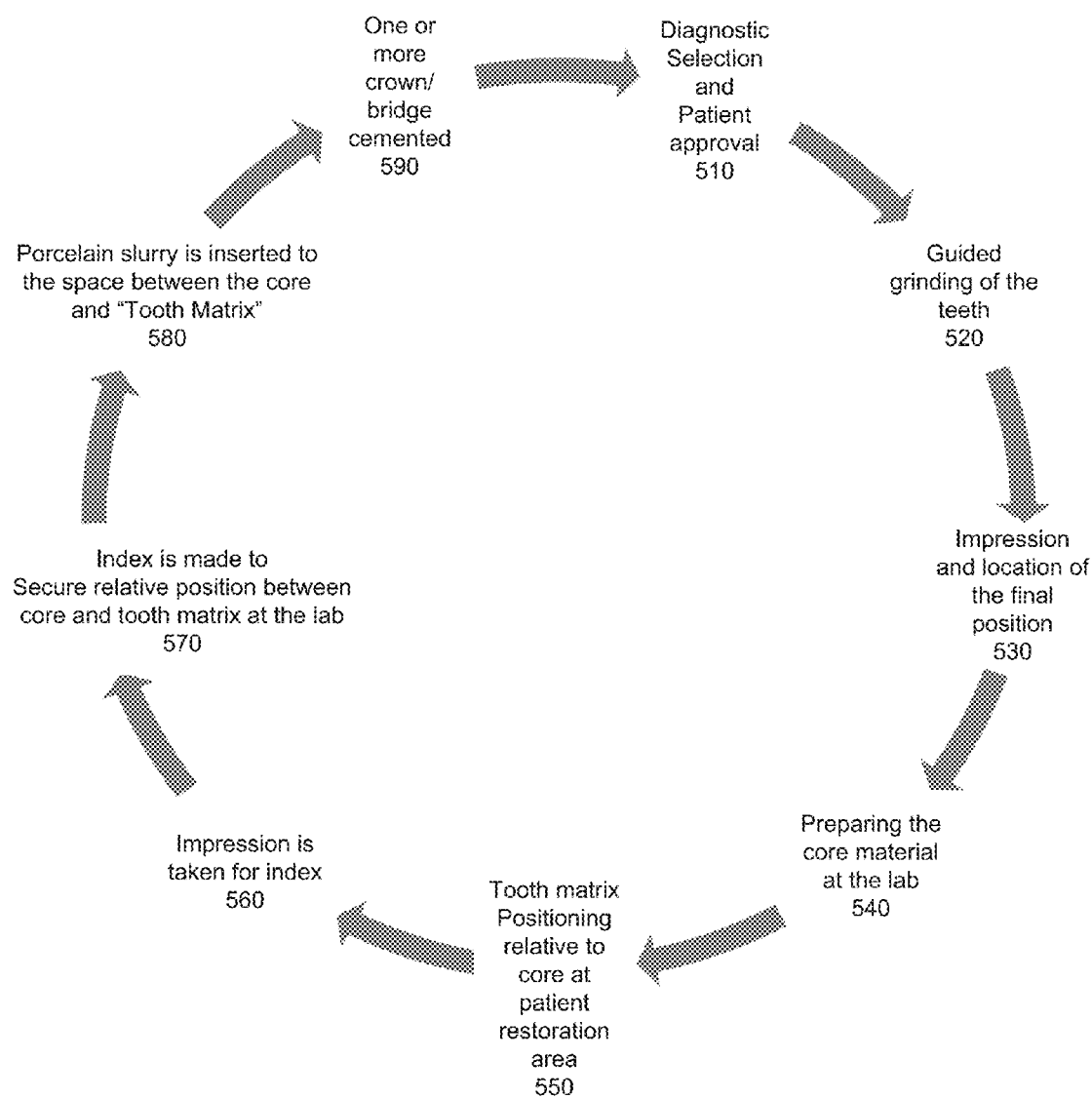
FIG. 12 illustrates a method according to an embodiment of the invention.

FIG. 12 illustrates method 500 according to an embodiment of the invention.

Method 500 includes a sequence of stages 510-520. The sequence can be executed one or more times.

Stage 510 includes performing a diagnostic stage and receiving the approval of the patient.

Stage 520 includes performing a guided grinding of the tooth.

Stage 530 includes performing an impression and finding the final location of the teeth matrix.

Stage 540 includes preparing the core material.

Stage 550 includes positioning the tooth matrix relative to the core at the patient restoration area.

Stage 560 includes taking an impression for an index.

Stage 570 includes making an index to secure relative position between core and tooth matrix.

Stage 580 includes inserting porcelain slurry to the space between the core and the tooth matrix.

Stage 590 includes cementing one or more crowns or bridges.

Method 500 can include a combination of the mentioned above methods.

According to an embodiment of the invention a method for producing a tooth matrix is provided.

Figure 13:
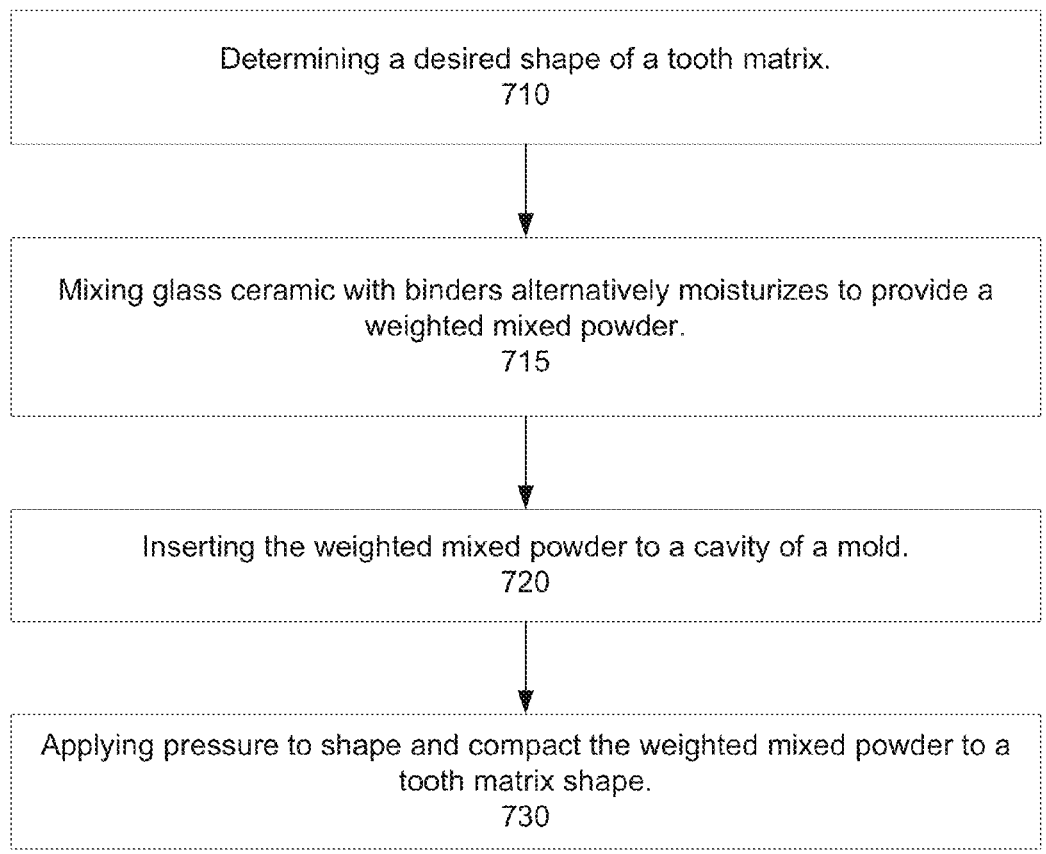
FIGS. 13-14 illustrate methods according to an embodiment of the invention.

FIG. 13 illustrated method 700 according to an embodiment of the invention.

Method 700 can include producing a tooth matrix that is made of materials known to the art of making dental prosthesis, glass ceramic. The method involves cold pressing or cold isostatic pressing, the advantage of cold pressing is its low price of production.

Method 700 starts by stage 710 of determining a desired shape of a tooth matrix. This can be performed by any of the previously mentioned methods.

Stage 710 is followed by stage 715 of mixing glass ceramic with binders (such as but not limited to poly vinyl alcohol in low percentage from 0.5%-5%) and moisturizes (such as but not limited to distilled water in percentage from 0.2%-6% and with or without lubricant like but not limited to glycerin). This provides a weighted mixed powder.

Stage 715 is followed by stage 720 of inserting the weighted mixed powder to the mold cavity.

Stage 720 is followed by stage 730 of applying pressure to shape and compact the powder to a tooth matrix shape, this stage can be done in single or multiple strokes to produce single or multiple layers.

Pressure Manipulation of powder like glass ceramic implies a big dilemma, which pressure to use in the manufacturing process, the nature of the glass ceramic powder is its wide range of materials. It typically includes 60% glass, 20% Al2O3 and 20% other metal oxides.

The different materials in the powder characterized in different resistant to pressure.

Applying high pressure can provide a more compact final product and better shape consistency. On the other hand it can cause changes in the desired shape and size of the different particles components in the compacted powder. The result of the particles changes would be unacceptable strength and most importantly the optical characteristics, when the glass breaks the translucency of the final product becomes opaque.

According to an embodiment of the invention stage 730 involves applying a pressure that is less than 0.5 GigaPascale. For example, the pressure can range between 0.0125 to 0.49 GigaPascale, This amount of pressure can be applied in any of the previously mentioned methods. For example—it can be applied during stage 320.

According to an embodiment of the invention a method for dental prosthesis buildup of one or more units with the combination of cad cam machine and prefabricated porcelain teeth shaped parts is provided.

For purpose of simplicity the description will relate to a single tooth, but the interest of the invention is the production of one or more teeth.

FIGS. 15-24 illustrate various cores, teeth, prefabricated teeth structures and the like. The functionality of these cores, and prefabricated teeth structures will be further illustrated below.

Figure 15:
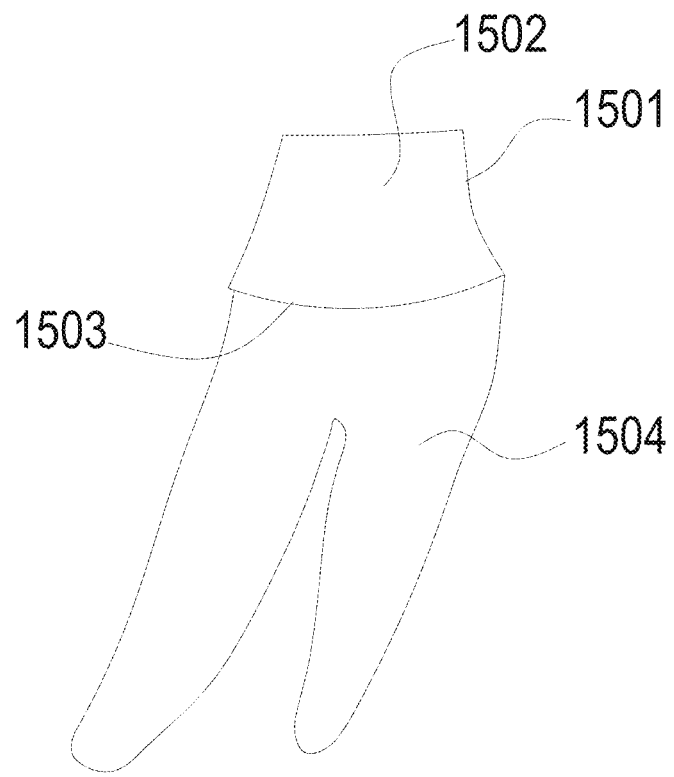
FIGS. 15-24 illustrate tooth matrixes, teeth and their surroundings and various components according to various embodiments of the invention.

FIG. 15 illustrates a treated teeth—it includes an upper portion 1502 that was sawn or otherwise processed in order to be connected to a core. The outer surface of the treated teeth is denoted 1501. The root of the teeth is denoted 1503.

Figure 16:
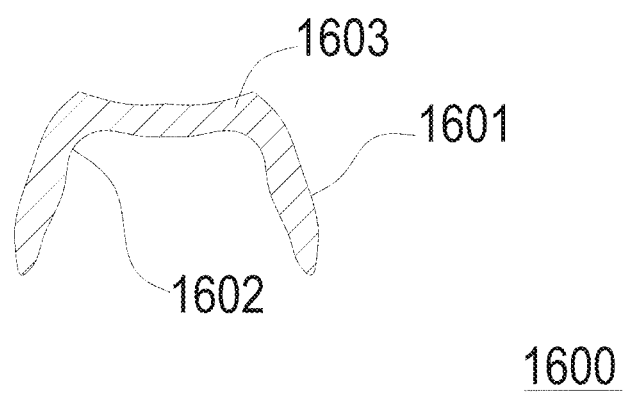

FIG. 16 illustrates a core 1600—it includes an upper portion 1603, a left portion 1602 and a right portion 1601.

Figure 17:
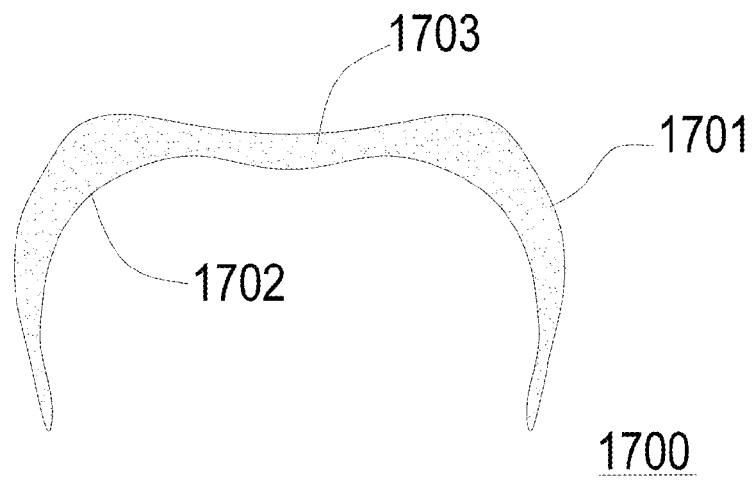

FIG. 17 illustrates a space 1700 between the outer surfaces of the core and an inner portion of a prefabricated teeth structure. This space can be filled by a ceramic material or other materials. The space includes an upper portion 1703, a left portion 1702 and a right portion 1701.

Figure 18:
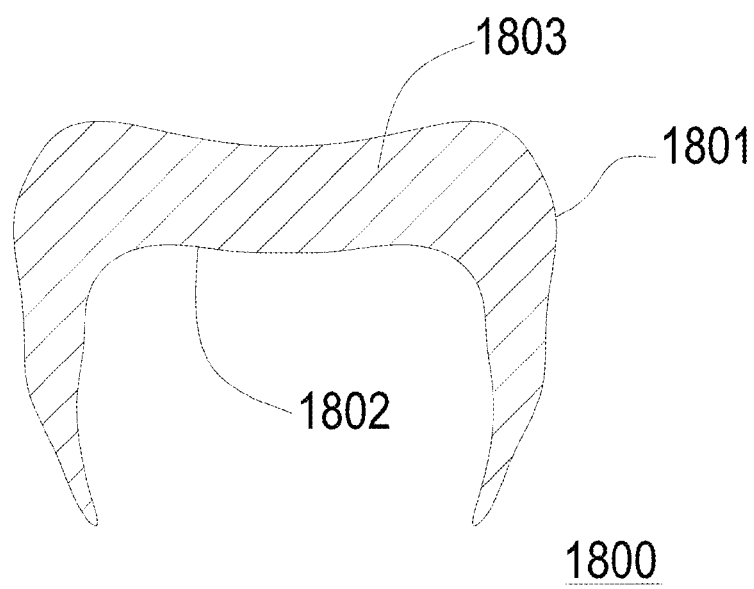

FIG. 18 illustrates a prefabricated teeth structure 1800 that has an inner portion 1802, an outer portion 1801 and a "body" 1803.

Figure 19:
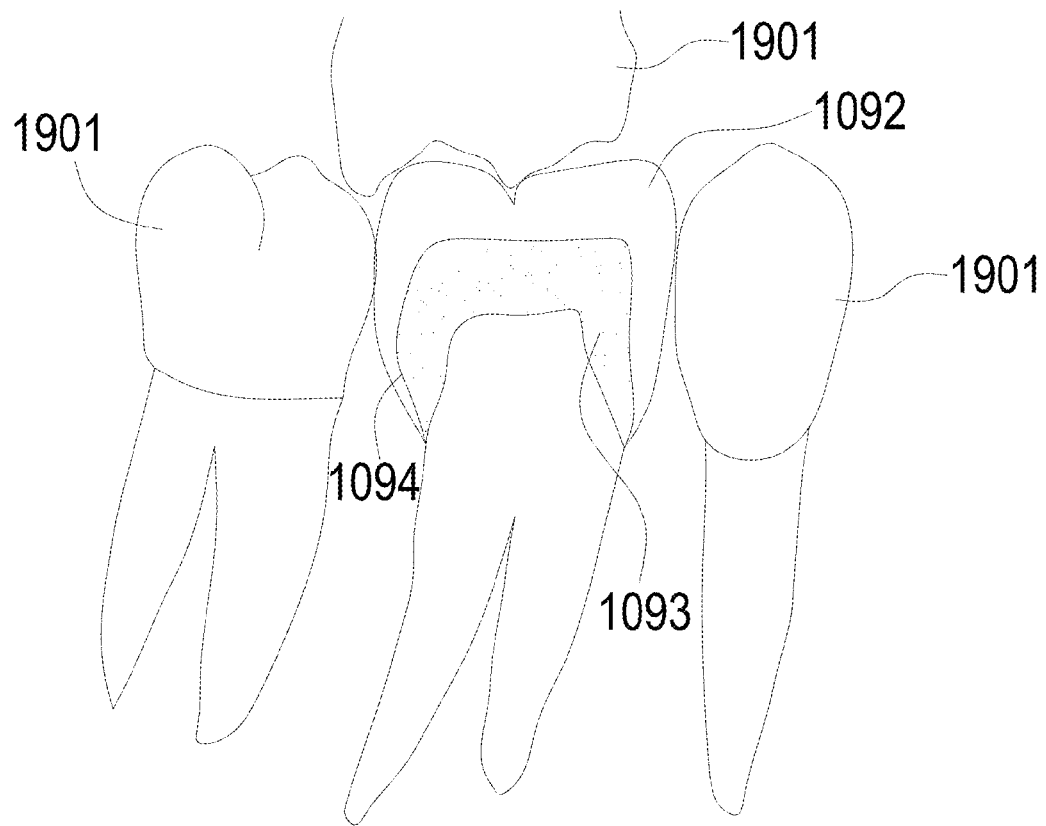

FIG. 19 illustrates core 1903, prefabricated tooth structure 1902, filling material 1904, a treated teeth and its surrounding—tooth 1901. FIG. 19 can provide an example of a treated tooth and its surroundings. The filling material fills the space 1904 between the outer portions of core 1903 and the inner portion of prefabricated tooth structure 1902.

Figure 20:
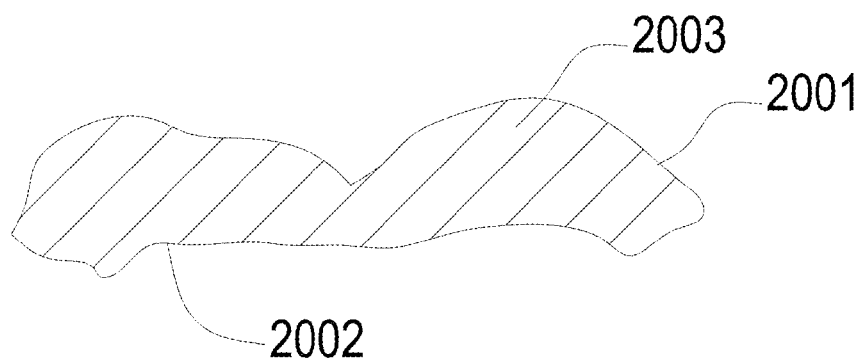
Figure 21:
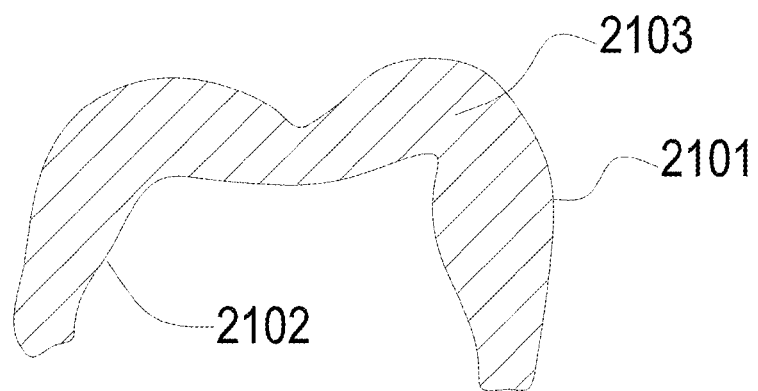

FIGS. 20 and 21 illustrate partial prefabricated tooth structures 2000 and 2100 that are designed to be smaller that the space defined between the teeth that surround a treated tooth and a core.

Partial prefabricated tooth structure 2000 has an inner portion 2002, an outer portion 2001 and "body" 2003.

Partial prefabricated tooth structure 2100 has an inner portion 2102, an outer portion 2101 and "body" 2103.

Figure 22:
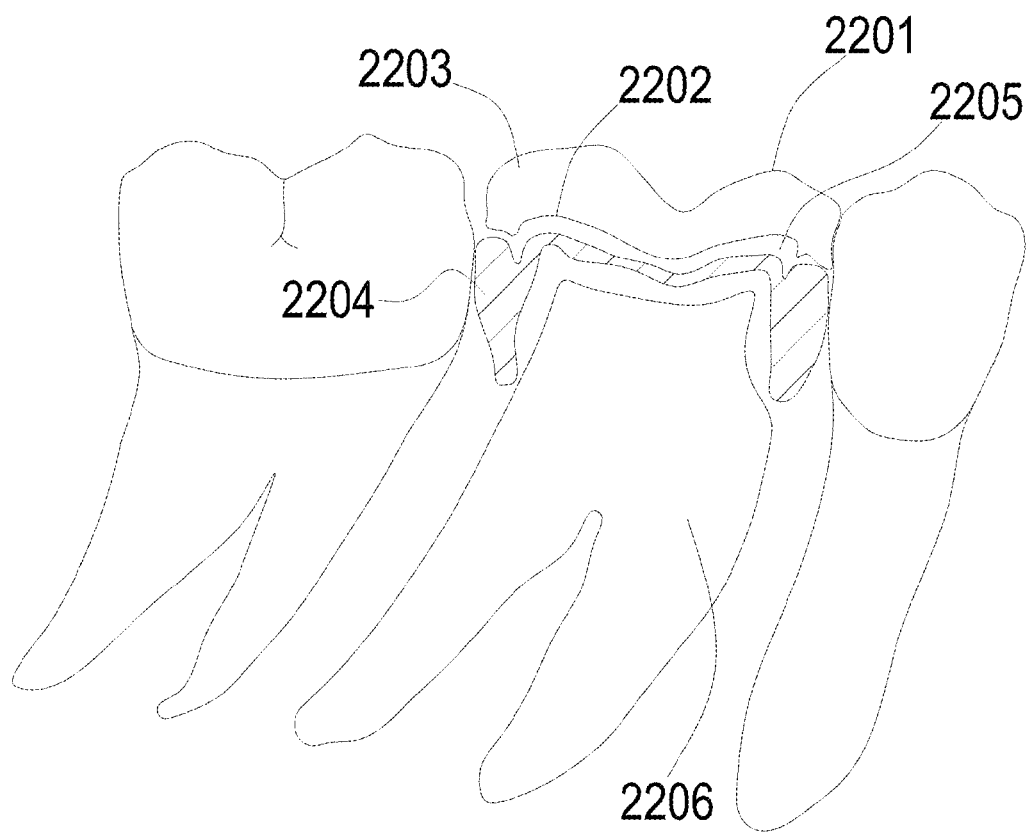
Figure 23:
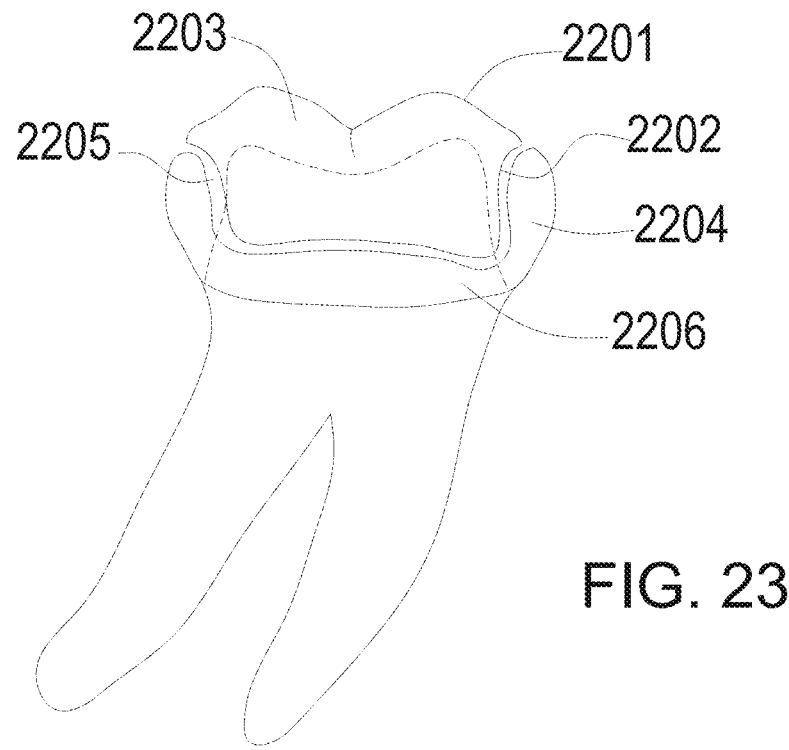
Figure 24:
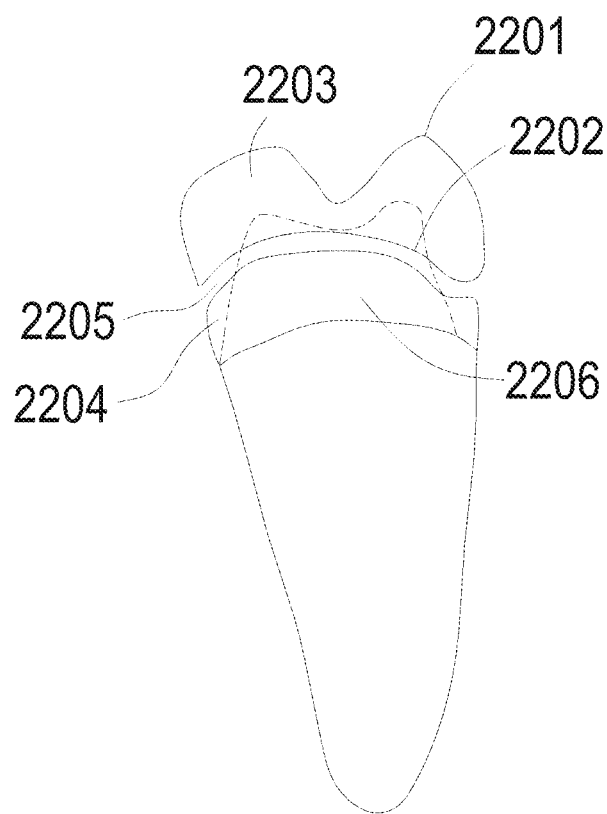

FIGS. 22, 23 and 24 illustrate core 2204, partial prefabricated tooth structure 2203, filling material 2205, a treated teeth 2206, and its surrounding. The outer surface (outer portion) of the partial prefabricated tooth structure is denoted 2203, the inner surface (inner portion) of partial prefabricated tooth structure 2203 is denoted 2202.

Core 2204 is fabricated such as to make contact with two adjacent teeth while the partial prefabricated tooth structure 2204 may be designed to contact an opposite teeth. Core 2204 can be fabricated by a computerized process (for example by a cad cam machine) while taking into account the space between adjacent teeth.

FIGS. 22 and 24 are cross sectional views taken along perpendicular axes. FIG. 23 is a side view of the treated teeth.

can provide an example of a treated tooth and its surroundings. The filling material fills the space 1904 between the outer portions of core 1903 and the inner portion of prefabricated tooth structure 1902.

Figure 14:
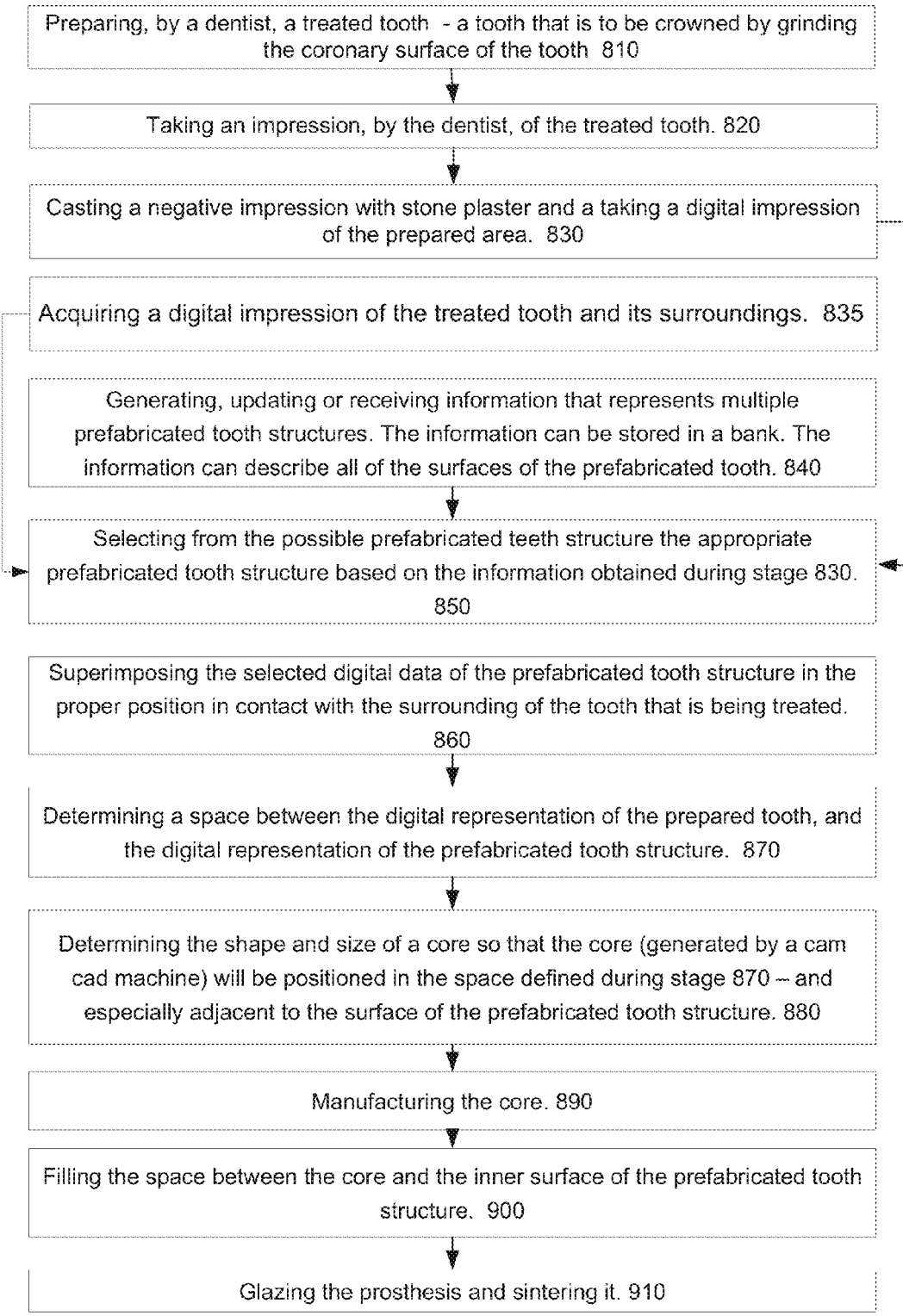

FIG. 14 illustrates method 800 according to an embodiment of the invention.

Method 800 includes (i) obtaining a digital data structure that includes information that represents a treated tooth to be crowned and a surroundings of the treated tooth (as illustrated by stages 830 and 835); (ii) selecting from multiple prefabricated teeth structures a selected prefabricated tooth structure based on the first space (as illustrated by stage 850); (iii) determining a space between a core and an inner portion of the selected prefabricated tooth (as illustrated by stage 850); (iv) filling the space between the core and the inner portion of the selected prefabricated tooth as illustrated by stage 900) and processing the core, to provide a prosthesis (as illustrated by stage 910). The method according to claim 37 comprising manufacturing the core by a computer aided machine.

Method 800 can include filling the space between the core and the inner surface of the prefabricated tooth structure while applying a pressure that is less than 0.5 GigaPascale, filling the space between the core and the inner surface of the prefabricated tooth structure by cold bonding materials, etching at least one outer surface of the core and etching at least one inner surface of the prefabricated tooth structure before filling the space between the core and the inner surface of the prefabricated tooth structure, and the like.

Method 800 starts by stage 810 of preparing, by a dentist, a tooth to be crowned by grinding the coronary surface of the tooth (FIG. 15) to decrease the size of the tooth about 1-4 mm from 5 surfaces of the tooth, occlusal, incisal, mesial, distal, buccal and lingual, the grinding takes place towards the root of the tooth (FIG. 15). The grinding preferably stops at the cervical finishing line which is above or below the gum line (FIG. 15). This tooth is also referred to as a treated tooth.

Stage 810 is followed by stage 820 of taking an impression, by the dentist, of the treated tooth.

Stage 820 is followed by either one of stages 830 and 835.

Stage 830 includes casting a negative impression with stone plaster of the treated tooth and its surroundings and acquiring a digital impression of the negative impression.

Stage 835 includes acquiring (for example—by the dentist) a digital impression of the treated tooth and its surroundings.

The outcome of either one of stages 830 and 835 is a digital file that represents the treated tooth and its surrounding. The digital file can be processed by automatic three dimensional engineering software.

Especially, the file represents the surrounding mesial and distal teeth, gingivae. Thus, a computer can process the digital file that stores information that represents the treated tooth surface and surrounding components surfaces.

FIG. 18 shows a prefabricated tooth structure. The prefabricated tooth structure has one or more layers that may give the prefabricated tooth structure an aesthetic appearance of a natural looking tooth. The prefabricated tooth structure can be made from glass ceramic with linear thermal coefficient factors that are appropriate to be sintered with the crown core material that are known to the prior art.

Method 800 also includes stage 840 of generating, updating or receiving information that represents a single and/or multiple prefabricated tooth structures. The information can be stored in a digital bank. The information can describe all of the surfaces of the prefabricated tooth structures.

The digital data of the prefabricated tooth structure (for example—those illustrated in FIG. 18) which was acquired during stage 840 and can be digitally stored in a teeth structure bank files in the Cad Cam computer data storage or any other form of digital storage including the internet.

Stages 830, 835 and 840 are followed by stage 850 of selecting from the possible prefabricated teeth structures the appropriate prefabricated tooth structure based on the information obtained during stage 830.

Stage 850 performs a selection from the bank files of the appropriate prefabricated tooth structure for the tooth to be restored. The selecting of stage 850 is based on the dimension for the crown as is dictated by the surrounding teeth, namely the mesial, distal and opposing teeth of the tooth to be restored with the said crown and/or bridge.

Stage 850 is followed by stage 860 of superimposing the selected (3D) digital data of the prefabricated tooth structure in the proper position in contact with the surrounding of the tooth that is being treated. The surrounding is defined by the mesial, distal and opposing teeth (illustrated in FIG. 19).

Stage 860 is followed by stage 870 of determining a space between the digital representation of the prepared tooth, and the digital representation of the prefabricated tooth structure. This space is bounded between the surface of the prepared tooth (element 1501 of FIG. 15) and the inner surface of the prefabricated tooth structure (FIG. 19, element 1902). The root of the treated teeth is illustrated as element 1504 in FIG. 15.

This space needs to include two components namely core structure (the core structure of FIG. 16 is illustrated as having an upper part 1603, a right part 1601 and a left part 1602) and intermediate structure (FIG. 17).

Stage 870 may include determining the space for the core structure (FIG. 16) from its inner (dental side) wherein this space is determined by the digital surface data of the treated tooth (also referred to as prepared tooth). Stage 870 may also include determining a space that spans from the outer side the core—based on the shape of the inner side of the prefabricated tooth structure.

Stage 870 is followed by stage 880 of determining the shape and size of a core so that the core (generated by a cam cad machine) will be positioned in the space defined during stage 870—and especially adjacent to the surface of the prefabricated tooth structure.

Stage 880 is followed by stage 890 of manufacturing the core.

Stage 890 is followed by stage 900 filling the space between the core and the inner surface of the prefabricated tooth structure. Stage 890 can include filling the space by cold bonding materials.

Stage 900 may include luting the core to the prefabricated tooth structure.

Stage 900 may include luting of the porcelain prefabricated tooth form to the cad cam core material. This stage can include cementation with cements that are known to the art.

Stage 890 can include etching surfaces outer surface of the core and etching inner surfaces of the prefabricated tooth structure. In this case stage 900 may include adding bonding material to the etched surfaces, and pouring luting material to the space cutoff the excess and light cure the luting material as the prefabricated tooth form is translucent and would allow using this technique.

Stage 900 may also include filling the space by wet powder porcelain.

Stage 900 is followed by stage 910 of glazing the prosthesis and sintering it. Stage 910 may include sintering in a temp of 600-1100 C.

Method 800 may include utilizing a partial prefabricated tooth structure (for example—see FIGS. 22, 23 and 24) that has at least one dimension that is smaller than the surrounding of the treated teeth. This prefabricated tooth structure is referred to as partial tooth structure as it is not intended to exactly fit the entire space defined by the surroundings of the treated tooth. In this case the core or filling materials can contact these adjacent tooth.

This partial prefabricated tooth structure (2000 of FIG. 20 or 2100 of FIG. 21) allows using mastication area from glass ceramic which is best suited to conform to the opposing natural enamel or glass ceramic of dental prosthesis in the hardness quality. This feature assists in preserving the opposing mastication area.

This partial prefabricated tooth structure can be designed to be short in mesial and distal contact points to allow the Cad Cam produced core contact point surfaces to be fitted to the mesial and distal teeth.

Method 800 and especially stage 850 can include selecting a partial prefabricated tooth structure that is short on the buccal and lingual sides (see: FIGS. 22 and 24). This allows the Cad Cam machine to produce a core shape that will fit to the mesial and distal contact points, the prepared tooth finishing lines (illustrated in FIG. 25) and will form a core which is in the shape of a tooth excluding the space of the mastication area, in this space the short adjustable prefabricated tooth structure will be fitted and cemented in the above mentioned methods.

If such a partial prefabricated tooth structure is selected then stage 900 can include binding between the partial prefabricated tooth structure and the core material by filling the space between the partial tooth structure and the core material with wet powder porcelain and to sinter in furnace at temperature of 600-1100 C.

Another method of producing a dental prosthesis using cad cam technology core and prefabricated porcelain tooth structure can also utilize wax that partially fills the gap between the core and the prefabricated tooth structure. The cad cam machine will select the appropriate size of the prefabricated tooth structure digital image for the treated tooth to be restored considering the border of the neighboring and opposing teeth. The computer will produce a core material which its inner side fits the tooth preparation side and the core outer side is distant from the inner digital representation of the prefabricated tooth structure when the prefabricated tooth structure in the correct positioning considering the neighboring teeth.

The dental technician will receive the fabricated core and will cover it with wax that will fill the gap between the selected prefabricated tooth structure and the core (instead of a space between the core and the entire space defined by the surroundings of the treated tooth.

Thus, a technician can apply wax on a core to fill a space between the core and the prefabricated teeth structure, fill the gap with wax, cause the wax to disappear by heat and them fill the space in which the wax resided by filling material such as a ceramic material that can be opaque.

In this case stage 900 can include heating a components that include the core, the prefabricated teeth structure and wax in order to remove the wax, and filling the space by a filling material.

This implementation of stage 900 allows a provision of a prosthesis that includes multiple layers that have different optical characteristics—it allows adding an additional aesthetic appearance to the lost wax procedure.

The different shape and size of teeth would be selected from the bank digital files, representing the prefabricated porcelain teeth forms with the aid of facial recognition software. In the impression taking session the dentist will take a digital image of the patient face, the face recognition software will define the outline of the face and will categorize the face into four categories; oval, round, square and triangular. According to the category the computer will select the appropriate shape of teeth from the bank teeth to harmonize with the facial outline.

In case of breakage of the prefabricated tooth structure from the dental prosthesis the replacement of the prefabricated tooth structure is a practical way to restore the prosthesis.

The prefabricated tooth structure is a shelf readymade with glazed and all the aesthetic is part of the prefabricated tooth structure ready for cementation; as such, it saves the time and labor needed for the buildup process.

The method can include: (i) Manufacturing prefabricated pieces to be applied on framework; (ii) Producing separate pieces in the cad cam machine; (iii) Sintering the parts in oven; (iv) Soldering pieces of framework; (v) Interconnections between pieces of framework; (vi) possible cementation between the parts.

The present invention can be practiced by employing conventional tools, methodology, and components. Accordingly, the details of such tools, component, and methodology are not set forth herein in detail. In the previous descriptions, numerous specific details are set forth, in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

The invention claimed is:

1. A method for preparing a permanent dental prosthesis for a patient, the method comprising:
   selecting a pre-fabricated tooth matrix having an enamel layer, that harmonizes with a facial outline of the patient, from a group of pre-fabricated tooth matrices of shapes and sizes that differ from each other according to categories of facial outline, said tooth matrices being manufactured as sets, wherein each said tooth matrix has an outer appearance of a tooth, has an enamel layer, and defines an inner cavity;
   after the step of selecting, grinding at least one tooth structure or implant in a mouth of the patient, according to a shape and size of the inner cavity of the selected tooth matrix so that the ground tooth structure or implant fits said inner cavity; and
   permanently attaching the selected pre-fabricated, tooth matrix to said ground tooth structure or implant by pouring a composite for porcelain between the ground tooth structure and the selected tooth matrix.

2. The method according to claim 1, wherein said step of grinding includes grinding at least one tooth structure or implant in a mouth of the patient according to a tooth grinding guide, said tooth grinding guide corresponding to said selected tooth matrix, wherein an outer portion of said tooth grinding guide is shaped like an outer surface of said corresponding tooth matrix, and wherein an inner portion of said tooth grinding guide is shaped like the inner cavity of the corresponding tooth matrix, to guide grinding of the patient's tooth structure or implant to fit said inner cavity.

3. The method according to claim 1, wherein the step of attaching includes attaching the tooth matrix by the composite for porcelain that is selected based upon a desired color of the prosthesis.

4. The method according to claim 1, further comprising illustrating to a patient an expected result of a restoration process by temporarily placing in the mouth of the patient the selected tooth matrix before said step of grinding.

5. The method according to claim 1, wherein said step of selecting includes:
   providing digital tooth matrix information of the patient's mouth to a computerized process; and
   selecting the appropriate shape of tooth matrix by the computerized process using face recognition software.

6. The method according to claim 2, wherein said grinding guide is designed to shape the remaining tooth structure or implant according to a shape and size of the inner cavity of the selected tooth matrix, the composite for porcelain and a core structure, and to a shape and a restoration area within the mouth of the patient.

7. The method according to claim 1, wherein:
   the step of selecting includes selecting a light transparent tooth matrix; and
   the step of attaching includes pouring the composite for porcelain of a selected color for bonding the tooth matrix to the element.

* * * * *